US 12,208,016 B2

(12) United States Patent
Biedermann et al.

(10) Patent No.: US 12,208,016 B2
(45) Date of Patent: Jan. 28, 2025

(54) IMPLANT, INSERTION DEVICE, AND PLATE ASSEMBLY

(71) Applicant: BIEDERMANN TECHNOLOGIES GMBH & CO. KG, Donaueschingen (DE)

(72) Inventors: Timo Biedermann, Trossingen (DE); Tobias Hägle, Donaueschingen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 2 days.

(21) Appl. No.: 17/479,376

(22) Filed: Sep. 20, 2021

(65) Prior Publication Data

US 2022/0087830 A1    Mar. 24, 2022

Related U.S. Application Data

(60) Provisional application No. 63/081,488, filed on Sep. 22, 2020.

(30) Foreign Application Priority Data

Sep. 22, 2020   (EP) ..................................... 20197497

(51) Int. Cl.
*A61F 2/44* (2006.01)
*A61F 2/46* (2006.01)

(52) U.S. Cl.
CPC ............ *A61F 2/442* (2013.01); *A61F 2/4455* (2013.01); *A61F 2/4611* (2013.01)

(58) Field of Classification Search
None
See application file for complete search history.

(56) References Cited

U.S. PATENT DOCUMENTS

| 8,673,012 B2 | 3/2014 | Smith et al. |
| 9,687,356 B1 | 6/2017 | Spangler et al. |

(Continued)

FOREIGN PATENT DOCUMENTS

| EP | 2 055 270 A1 | 5/2009 |
| EP | 2 992 846 A1 | 3/2016 |

(Continued)

OTHER PUBLICATIONS

Extended European Search Report for Application No. 19198123.2, dated Mar. 19, 2020, 9 pages.

(Continued)

*Primary Examiner* — Tessa M Matthews
(74) *Attorney, Agent, or Firm* — Lewis Roca Rothgerber Christie LLP

(57) ABSTRACT

An intervertebral implant includes a body having a first face, a second face connected to and opposite the first face, a width and a length at least as long as the width that extend around the first and second faces, and first and second connection portions for connecting the implant to a separate holding member. The first and second connection portions each includes a hollow space accessible from outside the body through an opening formed between the first and second faces. The openings are elongate and extend away from one another around the implant from a same first side that defines the length of the body to respective second and third sides opposite to one another that define the width of the body, and are arranged such that the first and second connection portions are simultaneously engageable by the holding member.

24 Claims, 16 Drawing Sheets

(56) References Cited

U.S. PATENT DOCUMENTS

| | | |
|---|---|---|
| 2005/0101960 A1 | 3/2005 | Fiere et al. |
| 2005/0096745 A1 | 5/2005 | Andre et al. |
| 2006/0229627 A1 | 10/2006 | Hunt et al. |
| 2008/0051890 A1 | 2/2008 | Waugh et al. |
| 2009/0112220 A1 | 4/2009 | Kraus |
| 2010/0268279 A1* | 10/2010 | Gabelberger ...... A61B 17/7037 606/278 |
| 2011/0264218 A1 | 10/2011 | Asaad |
| 2011/0276142 A1 | 11/2011 | Niemiec et al. |
| 2012/0165943 A1 | 6/2012 | Mangione et al. |
| 2012/0209383 A1 | 8/2012 | Tsuang et al. |
| 2014/0135930 A1* | 5/2014 | Georges ............. A61F 2/4455 623/17.16 |
| 2015/0100126 A1* | 4/2015 | Melkent ............ A61B 17/8042 623/17.16 |
| 2015/0190241 A1* | 7/2015 | Gowan ............... A61F 2/447 623/17.16 |
| 2016/0235546 A1 | 8/2016 | Cheng et al. |
| 2017/0056194 A1* | 3/2017 | Biedermann ........... A61F 2/442 |
| 2017/0100260 A1 | 4/2017 | Duffield et al. |
| 2017/0172759 A1 | 6/2017 | Kukkar et al. |
| 2017/0231782 A1* | 8/2017 | Perez-Cruet ......... A61F 2/4611 623/17.12 |

FOREIGN PATENT DOCUMENTS

| | | |
|---|---|---|
| EP | 3 135 254 A1 | 3/2017 |
| FR | 2 822 674 A1 | 10/2002 |
| FR | 2 948 277 A1 | 1/2011 |
| JP | 2013-509940 A | 3/2013 |
| WO | WO 2008/085521 A1 | 7/2008 |
| WO | WO 2011/056172 A1 | 5/2011 |
| WO | WO 2015/081142 A1 | 6/2015 |

OTHER PUBLICATIONS

Extended European Search Report for Application No. 20197497.9, mailed Mar. 12, 2021, 11 pages.

* cited by examiner

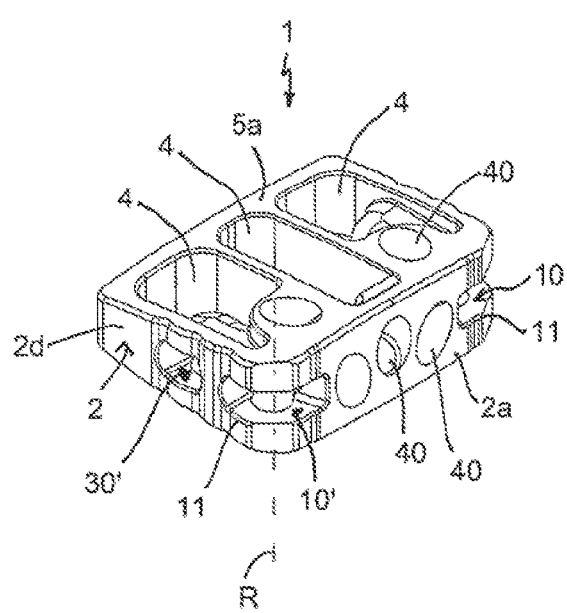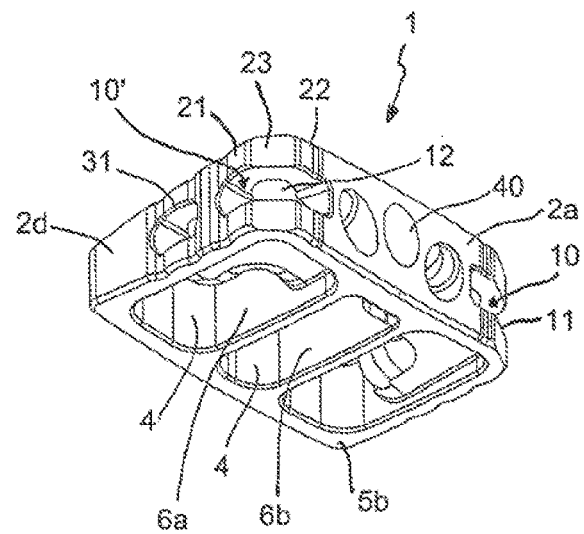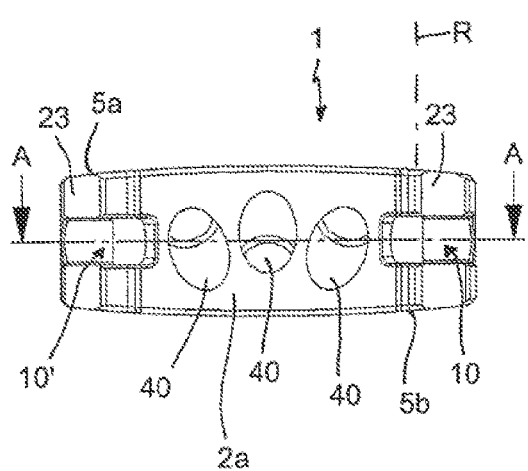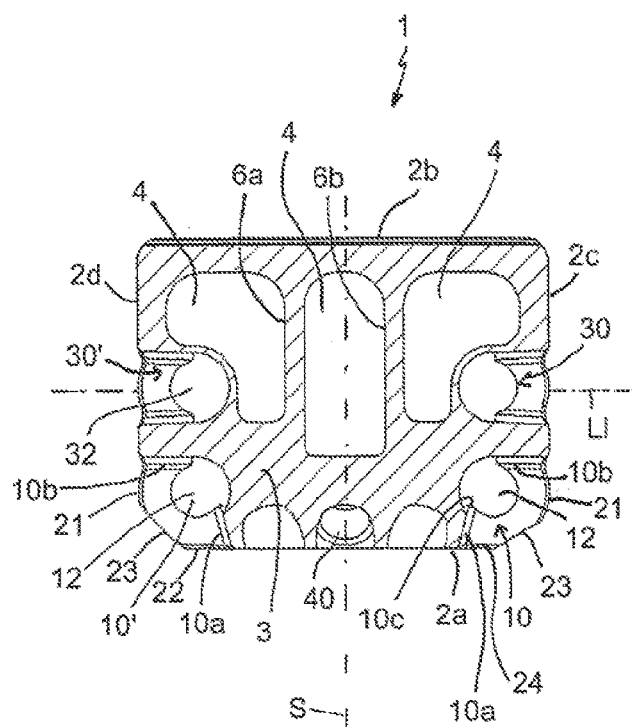
Fig. 2
Fig. 3
Fig. 4
Fig. 5

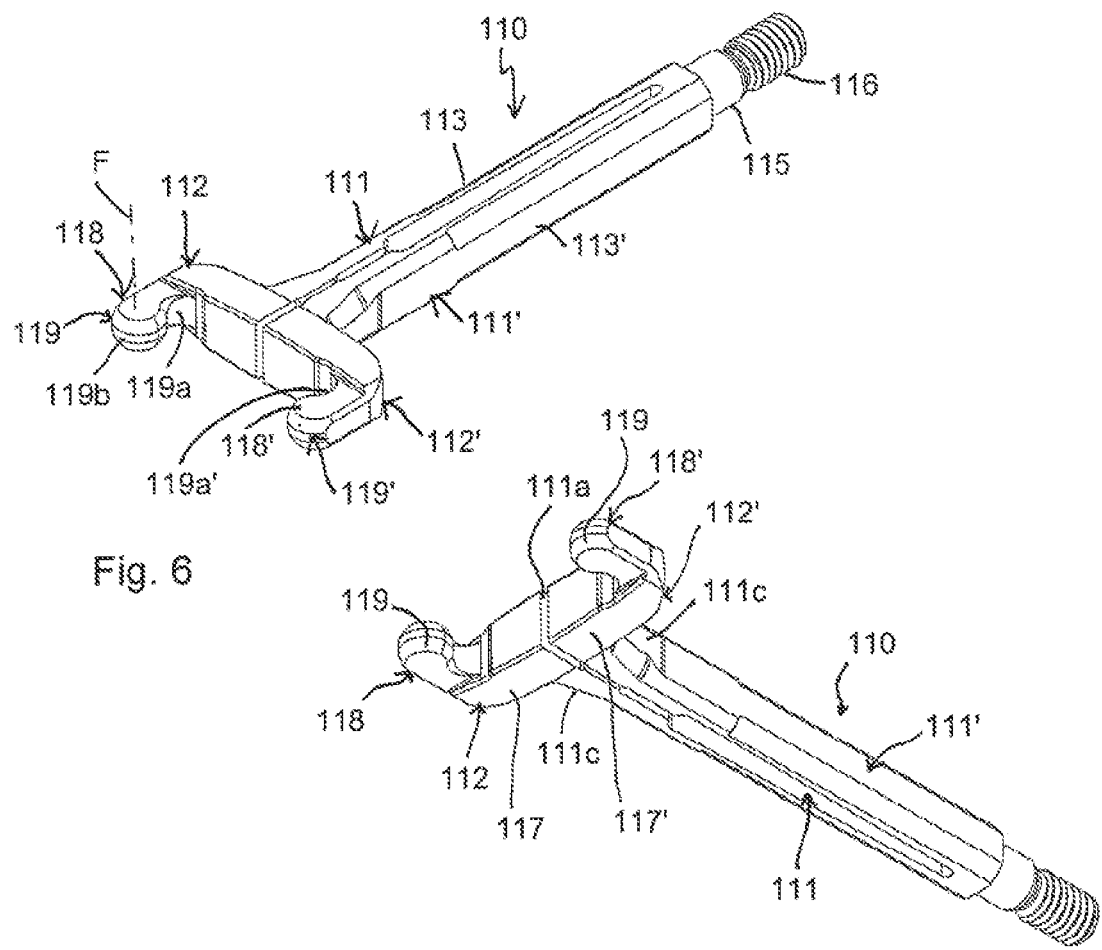
Fig. 6
Fig. 7
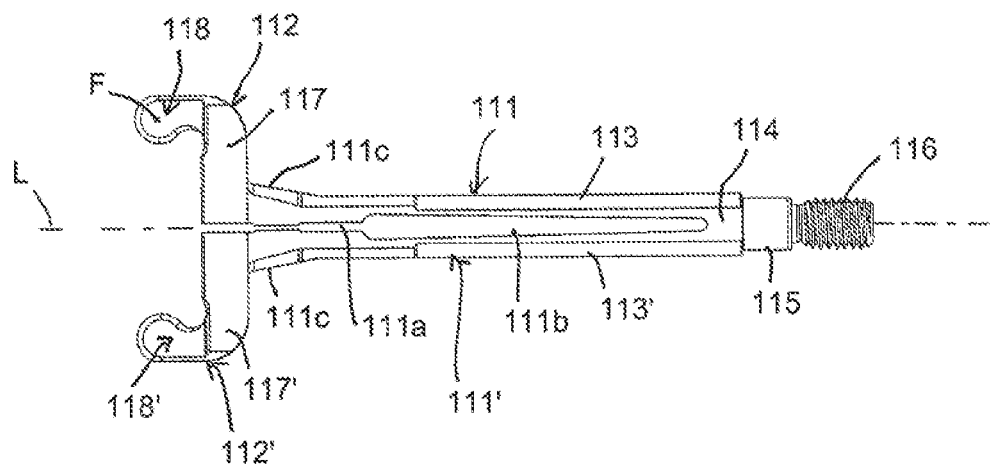
Fig. 8

IMPLANT, INSERTION DEVICE, AND PLATE ASSEMBLY

CROSS-REFERENCE TO RELATED APPLICATION(S)

The present application claims priority to and the benefit of U.S. Provisional Patent Application No. 63/081,488, filed Sep. 22, 2020, the contents of which are hereby incorporated by reference in their entirety, and claims priority from European Patent Application EP 20 197 497.9, filed Sep. 22, 2020, the contents of which are hereby incorporated by reference in their entirety.

BACKGROUND

Field

The application relates to an implant, in particular to a spinal implant, an insertion device for such an implant, and a plate assembly. The implant may be, for example, an intervertebral implant for replacing a damaged intervertebral disc or a placeholder for bridging the space of a removed vertebra following vertebrectomy.

Description of Related Art

In the case of damaged intervertebral discs, lumbar or thoracic interbody fusion surgery is one of the most commonly performed instrumented spinal fusion surgeries. Among others, known surgical approaches for interbody fusion of the lumbar spine include posterior lumbar interbody fusion (PLIF), transforaminal lumbar interbody fusion (TLIF), anterior lumbar interbody fusion (ALIF), anterolateral ALIF, and lateral interbody fusion, as well as oblique lateral interbody fusion.

An intervertebral implant and a device for inserting the same that are, for example, suitable for TLIF are described in US 2017/0056194 A1. The intervertebral implant has a top surface, a bottom surface, a sidewall extending between the top surface and the bottom surface, and a hollow space formed within the intervertebral implant and accessible through an elongate opening extending through a recessed portion of the sidewall. The hollow space is shaped to receive an engagement portion of a drive shaft of an insertion tool. The intervertebral implant includes at least two guiding surfaces facing each other and being configured for sliding engagement by a portion of a sleeve of the insertion tool movably holding the drive shaft.

US 2016/0235546 A1 describes a spacer with temporary fixation which includes the spacer, a plate, an attachment member, and a temporary fixation screw. The temporary fixation of the spacer is applicable in a lateral spinal procedure to prevent migration of the spacer while a patient is being rotated after insertion of the spacer.

SUMMARY

It is an object underlying the invention to provide an improved or alternative implant, an insertion device therefor, and a fixation device, and systems including the implant and an insertion device or a fixation device, such as a plate assembly, that are versatile and simple to use and have an enlarged field of application.

According to an embodiment, an implant, in particular a spinal implant, for example an intervertebral implant or a placeholder for vertebrae, includes a body insertable into the space between two bones or bone parts, more particularly between two vertebrae, the body including a first face, a second face connected to and opposite to the first face, and at least one connection portion for connecting the spinal implant to a holding member of an insertion device for the implant or a secondary device such as a plate member. The connection portion has a hollow space defined by the body between the first and second faces configured to accommodate an engagement portion of the holding member, the hollow space being accessible from outside the body through an opening formed between the first and second faces. The opening is elongate with a length that is greater than a width in at least a portion thereof such that the engagement portion of the holding member is insertable into the hollow space through the opening when the engagement portion has a first orientation and is prevented from removal from the hollow space when the engagement portion is in a second orientation. The connection portion is located on the implant and configured to selectively connect at least two different holding members to the implant.

The connection portion of the implant is multi-functional. The connection portion is designed such that a holding portion of a further device, such as an insertion instrument or a plate member, which is adapted to cooperate with the connection portion, can be inserted and tilted, whereafter the further device is prevented from removal. In addition, other instruments, such as a different insertion device which is suitable for a different surgical insertion approach, may be connected to the implant using the connection portion in a different manner.

The connection is threadless, which renders it robust and easy to establish, disconnect, and reconnect.

The implant may be an intervertebral implant for disc replacement or a placeholder for bridging a gap formed after removal of one or more vertebrae or portions thereof.

Due to the increase in functionality, the implant may be particularly useful in the case of difficult anatomical circumstances, such as anterior and lateral approaches to the spine, as well as revision surgery.

According to a further embodiment, an insertion device for inserting the implant described above includes two holding members each having an engagement portion, wherein the holding members form a fork-shaped holding portion of the insertion device and wherein the engagement portions are configured to engage connection portions provided at opposite corners of the implant, respectively. The holding members are configured to move from a first configuration in which the engagement portions have a first distance from each other to a second configuration in which the engagement portions have a second distance from each other that is smaller than the first distance. A sleeve may be provided around the holding members and may be displaceable relative to the holding members to move the holding members from the first configuration to the second configuration.

With such an insertion device, the implant, in particular an intervertebral implant, may be engaged in a clamp like manner and fixed by the instrument. The implant may then be inserted, for example, using an anterior approach.

According to a further embodiment, a plate assembly includes a plate member and a holding member connectable to the plate member, wherein the holding member includes an engagement portion that is configured to engage the connection portion of the implant in a threadless manner. In particular, the plate member may be used as a temporary fixation plate which can provide temporary stability to the spinal region which includes the implant.

The threadless connection may also permit the plate member to assume various angular positions relative to the implant.

According to a still further embodiment, the implant includes a tube member with openings therein which is intended to form a placeholder for one or more removed vertebrae or portions thereof. The hollow space of the connection portion is formed inside the tube.

According to a still further embodiment, a kit of an implant as described above includes at least two devices selected from a group of at least two different insertion devices as described hereinafter and a plate assembly.

BRIEF DESCRIPTION OF THE DRAWINGS

Further features and advantages will become apparent from the detailed description of embodiment by means of the accompanying drawings. In the drawings:

FIG. 2 shows a perspective view from a top of the intervertebral implant of FIG. 1.

FIG. 3 shows a perspective view from a bottom of the intervertebral implant of FIGS. 1 and 2.

FIG. 4 shows a front view of the intervertebral implant of FIGS. 1 to 3.

FIG. 5 shows a cross-sectional view of the intervertebral implant of FIGS. 1 to 4, the cross-section taken along line A-A in FIG. 4.

FIG. 6 shows a perspective view from a top of a holding portion of the insertion device of FIG. 1.

FIG. 7 shows a perspective view from a bottom of the holding portion of FIG. 6.

FIG. 8 shows a top view of the holding portion of FIGS. 6 and 7.

DETAILED DESCRIPTION

Figure 1:
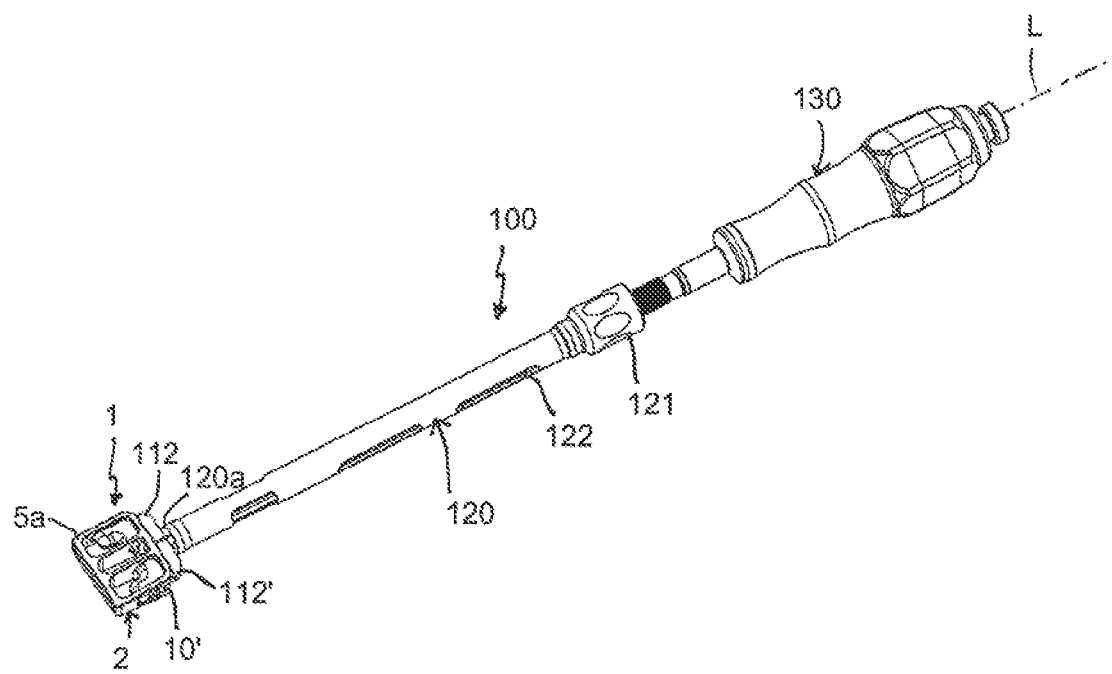
FIG. 1 shows a perspective view of a first embodiment of a spinal implant in the form of an intervertebral implant, in particular for an ALIF-procedure and/or antero-lateral ALIF procedure, and a first insertion device.

FIG. 1 shows a perspective view of a spinal implant in the form of an intervertebral implant 1 and an insertion device 100 for inserting the intervertebral implant 1 into an intervertebral space. The intervertebral implant 1 shown in the figures may be used in particular for anterior lumbar interbody fusion (ALIF). However, the embodiment is not limited to this type of intervertebral implant. Referring in more detail to FIGS. 2 to 5, the intervertebral implant 1 has a body including a substantially vertical side wall 2. The side wall 2 is formed monolithically with an inner solid portion 3 and encloses one or more inner solid hollow spaces 4. The hollow spaces 4 are open towards an upper face 5a and a lower face 5b of the intervertebral implant 1.

In greater detail, the side wall 2 is formed by a front wall 2a, an opposite back wall 2b, a right side wall 2c, and a left side wall 2d, which are monolithically formed, such that the right and left side walls connect the front wall 2a and the back wall 2b with each other. The front wall 2a represents an anterior wall and the back wall 2b represents a posterior wall of the intervertebral implant 1. The front wall 2a and the back wall 2b may be longer than the right side wall 2c and the left side wall 2d, so that the intervertebral implant 1 may have an elongate outer contour. In the embodiment shown, the front wall 2a and the back wall 2b are substantially parallel to each other and define a longitudinal central axis LI of the intervertebral implant. Moreover, the front wall 2a and the back wall 2b may have different heights, such that the top face 5a and the bottom face 5b form an angle, resulting in the intervertebral implant 1 having a wedge shape. For example, the front wall 2a may have a height greater than that of the back wall 2b for the correction of lordosis.

Optionally, inner walls 6a, 6b may extend from the front wall 2a to the back wall 2b, which separates the hollow spaces 4 from each other. In the embodiment shown, three such hollow spaces 4 are provided, however, the design of the intervertebral implant is not limited to this number. The inner walls 6a, 6b may by symmetric with respect to a sagittal plane S that extends vertically through the centers of the front wall 2a and the back wall 2b. The solid portion 3 extends from the front wall 2a to a distance from the back wall 2b, and has a length in this direction such that connection portions in the form of recesses, as further described below, can be formed in the solid body 3 with depths sufficient for engagement with the insertion device 100. The hollow spaces 4 are configured to be filled with bone graft material or biologics. Further, engagement portions, for example teeth (not shown), may be provided in the upper face 5a and/or the lower face 5b of the intervertebral implant 1, which may facilitate penetration into the end plates of adjacent vertebral bodies.

At the corners that are formed by the transition of the front wall 2a to the left side wall 2d and to the right side wall 2c, recesses 10, 10', respectively are provided that each form an elongate opening 11 in the side wall 2. Each recess 10, 10' defines a connection portion configured for connection with a holding portion of an insertion device or a plate member.

The two recesses 10, 10' are mirror symmetrical with respect to the sagittal plane S, and therefore in the following, only the recess 10 will be described in more detail while in the embodiment, the recess 10' at the opposite corner has a mirror symmetrical design. The recess 10 defines a hollow space within the intervertebral implant 1 for receiving a portion of the insertion device. The recess 10 extends into the solid portion 3 and forms a corner with an angle of slightly more than 90° therein. Thereby, left and right boundary walls 10a, 10b of the recess 10 form an angle of slightly more than 90°, for example about up to 100°. The recess 10 and the opening 11 may be provided at a middle of the side wall 2 in the height direction. It shall be understood that the angle may also be about or exactly 100°.

A width of the recess 10 in the height direction is such that an engagement portion of the insertion device 100 can be introduced in one orientation, but cannot be introduced in a tilted orientation. Top and bottom walls of the recess 10 may be planar, and may extend substantially parallel to each other and substantially perpendicular to a vertical extension of the side wall 2 between the upper and lower faces 5a, 5b. The opening 11 extends in a circumferential direction from the front wall 2a over the corner between the front wall 2a and the right side wall 2c into the right sidewall.

In the inside corner of the recess 10, a spherically-shaped recess 12 is formed that is configured to receive an engagement portion of the insertion device 100. As shown in more detail in FIGS. 11c and 11d, a radius of the spherically-shaped recess 12 matches a radius of an outer surface of the engagement portion of the insertion device. An axis R extending through a center of the spherically-shaped recess 12 and parallel to the vertical extension of the side wall 2 forms an axis of rotation and more specifically, a pivot axis that enables a pivotal movement between the intervertebral implant 1 and an engagement portion of an insertion device or a plate member, as explained in greater detail below. The boundary walls 10a, 10b that delimit the recess 10 at the end of the opening 11 in the circumferential direction may have a contour that is suitable for guiding engagement with the engagement portion. The boundary walls may be, for example, substantially cylindrical. The boundary wall 10b is substantially perpendicular to the right side wall 2d and the boundary wall 10a extends at a slight angle to the front wall 2a in such a manner that an enlarged portion 10c may formed between the spherical recess 12 and the boundary wall 10a. By means of this, the insertion of the engagement portion of the insertion device may be more easily facilitated.

In addition, the side wall 2 may have, in the region of the elongate opening 11, outer surfaces that are shaped to provide abutment surfaces for an insertion device to achieve a form-fit engagement and/or to provide guiding surfaces for pivotal movement of the insertion device. As depicted in greater detail in FIG. 5, a first abutment surface 21 is provided around the lateral edge of the elongate opening that extends into the right side wall 2c. For the recess 10' the first abutment surface 21 is in the left sidewall 2d. The first abutment surface 21 may be substantially cylindrical with a cylinder axis substantially parallel to the axis of rotation R. A second substantially planar abutment surface 22 is provided around the opposite lateral edge of the elongate opening 11 that extends into the front wall 2a. Lastly, a third substantially planar abutment surface 23 may extend around substantially a center of the opening 11 and forms an angle of substantially 45° with the second abutment surface 22.

Optionally, the intervertebral implant 1 may include further connection portions in the side wall 2. In the embodiment shown, the intervertebral implant has additional recesses 30, 30' at the right side wall 2c and the left side wall 2d, respectively. Each recess 30, 30' defines an elongate opening 31 and has an inner spherically-shaped recess 32, permitting rotation of an inserted engagement portion therein. The recesses 30, 30' are each configured such that an engagement portion of a holding member of an insertion device or a plate member can be inserted in one orientation, but cannot be inserted in a tilted orientation. The connection portions 30, 30' permit only a single angle between the implant and the holding portion of the device to be attached. It shall be noted that the connection portions 30, 30' may also be designed such as to allow a variation in the angle between the insertion device and the implant.

Optionally, one or more additional holes 40 may be provided in the front wall 2a. The additional holes may be threaded, to receive fixation screws (not shown) for additional fixation of the intervertebral implant 1 with respect to the adjacent vertebral bodies. The axes of the additional holes 40 may be inclined with respect to the top face 5a and the bottom face 5b, so that fixation screws extending therethrough are configured to engage the end plates of the vertebral bodies, respectively.

It shall be noted that the number and position of the recesses and holes is not limited to the number and position shown in the embodiment, but more or less recesses and holes may be provided and the positions may vary.

Turning now to FIGS. 1 and 6 to 8, the insertion device 100 will be described. The insertion device 100 includes a holding portion 110, a sleeve 120 configured to extend around the holding portion 110, and a handle 130 connected to the holding portion. The sleeve 120 defines a longitudinal axis of the insertion device 100. The holding portion 110 includes two holding members 111, 111', the front portions 112, 112' of which form a fork-shaped clamp configured to engage the intervertebral implant 1. The holding members 111, 111' each includes a longitudinal bar 113, 113', wherein the bars 113, 113' are connected at their rear end 114. From the rear end 114, a post 115 with a threaded end portion 116 extends. The front portions 112, 112' each include a cross-bar 117, 117' extending transverse to the longitudinal axis in an outward direction. From each outer end of the cross-bar 117, 117', an engagement portion 118, 118' extends in a direction substantially parallel to the longitudinal axis L. The cross-bars 117, 117' may have a substantially rectangular cross-section with a height that is preferably smaller than a height of the front wall 2a. The length of the cross-bars 117, 117' is such that the engagement portions 118, 118' can be inserted into the recesses 10, 10'.

The engagement portions 118, 118' have a substantially spherical segment-shaped end portion 119, 119' with upper and lower surfaces that are substantially flat and parallel to each other. An axis F perpendicular to the flat surfaces is substantially perpendicular to the longitudinal axis L. The outer surface of the spherical segment-shaped end portions 119, 119' may have a small cylindrical portion 119b. Hence, the engagement portions 118, 118', and in particular the spherical-segment-shaped end portions 119, 119', have a flattened shape with a thickness slightly smaller than a vertical height of the elongate opening 11 to permit insertion of the engagement portion into the recess 10, 10'. Between the spherical segment-shaped end portions 119, 119' and the cross-bars 117, 117', the engagement portions 118, 118' include a narrowing section 119a, 119a' to provide a hook-like shape. The enlarged portion 10c may facilitate the engagement of the engagement portion with the recess 10, 10', respectively, since the spreading apart of the engagement portions required for entering the recesses may be reduced.

The holding members 111, 111' are separated by a slot 111a that may have a widened section 111b adjacent to the end portion 114. The slot 111a renders the holding members 111, 111' deflectable towards each other and apart from each other in a resilient manner. An outer surface portion 111c of the holding members 111, 111' adjacent to the cross-bars 117, 117' may be tapered and widen towards the cross-bars 117, 117'. When the sleeve 120 moves towards the cross-bars 117, 117', this results in compression of the holding members 111, 111' towards each other, which narrows the slot 111a and brings the engagement portions 118, 118' closer towards each other.

The sleeve 120 is configured to extend around the bar-shaped longitudinal portions 113, 113' of the holding portion. The sleeve includes a front end 120a and a rear end with a grip section 121, and an inner thread (not shown), for example in the region of the grip section 121 that is configured to cooperate with the threaded end portion 116 of the holding portion 110. Hence the sleeve 120 is configured to be moved forward and backward in the longitudinal direction by rotating the sleeve relative to the holding portion 110. When the sleeve is in the retracted position, its front end 120a has a distance from the cross-bars 117, 117' of the holding member 110 such that the tapered section 111c is at least partially exposed. An inner wall 120c adjacent to the front portion 120a of the sleeve 120 slightly tapers outward (see FIGS. 11a to 11d). This enables sliding of the sleeve over the tapered portion 111c. Moreover, longitudinal holes 122 may be provided in the sleeve that may serve for saving weight and/or facilitating cleaning. In a modification, the sleeve 120 may be moved forward and backward by pushing it relative to the holding portion 110.

The insertion device is configured to have a first configuration in which the engagement portions 118, 118' are spaced apart from each other at a first distance and a second configuration in which the engagement portions 118, 118' are spaced apart at a second distance smaller than the first distance. In the first configuration the sleeve is at the retracted position. By displacing the sleeve along the longitudinal axis L the slot 111a is narrowed so that the engagement portions 118, 118' are moved towards each other.

Parts and portions of the intervertebral implant and the insertion device may be made of any material, preferably, however, of a bio-compatible material, such as titanium or stainless steel, or of any other bio-compatible metal or metal alloy, or of a plastic material. For bio-compatible alloys, a NiTi-alloy, for example Nitinol, may be used. Other materials that can be used are Magnesium or Magnesium alloys, and bio-compatible plastic materials that can be used may be for example, Polyether ether ketone (PEEK) or Poly-L-lactide acid (PLLA). The parts can be made of the same or of different materials from one another.

Figure 9:
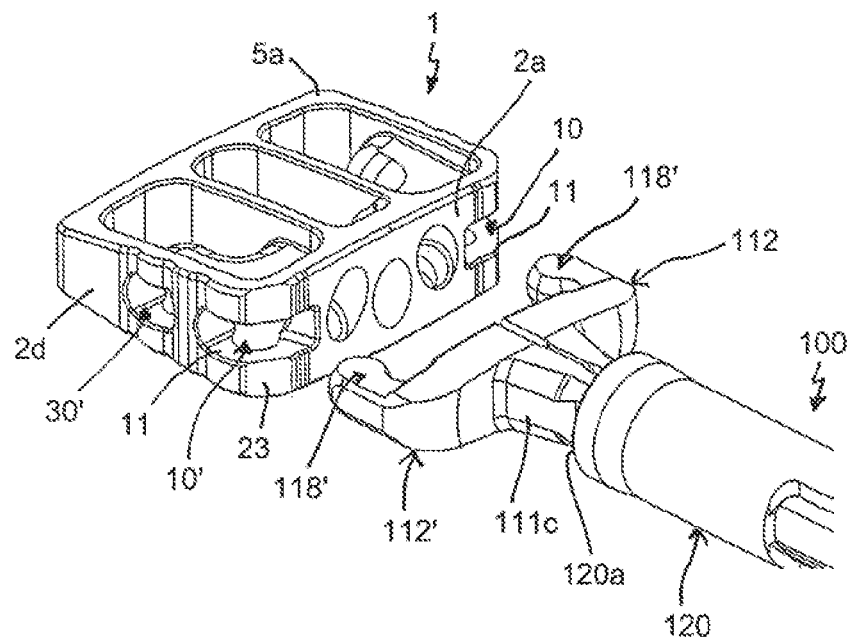
FIG. 9 shows a perspective view of a step of orienting the insertion device and the intervertebral implant of FIG. 1 relative to each other for connecting them.

Next, the operation between the intervertebral implant 1 and the insertion device will be explained. As shown in FIG. 9, the intervertebral implant is oriented with respect to the insertion device in such a manner that the front portion of the insertion device faces the front wall 2a of the intervertebral implant 1. The sleeve 120 is in the retracted position, where the tapered section 111c of the holding portion 110 is substantially free.

Figure 10:
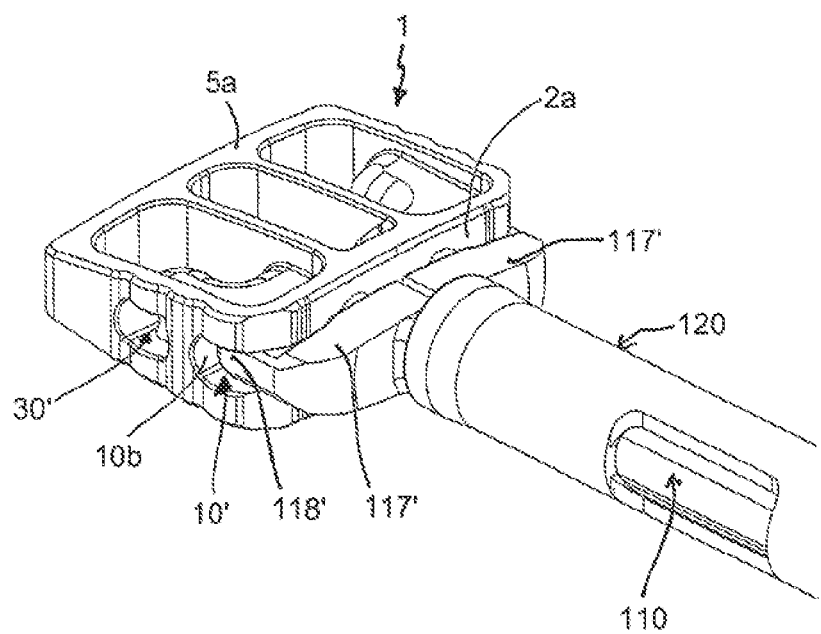
FIG. 10 shows a perspective view of a step of engaging the intervertebral implant of FIG. 9 with the insertion device.

FIG. 10 shows the connected configuration in which the engagement portions 118, 118' have engaged the spherical recess 12 inside the recesses 10, 10'. In this configuration, the sleeve 120 has been moved towards the cross-bars 117, 117' over at least a part or most of the tapered portion 111c so that the two engagement portions 118, 118' are pressed towards each other.

Figure 11:
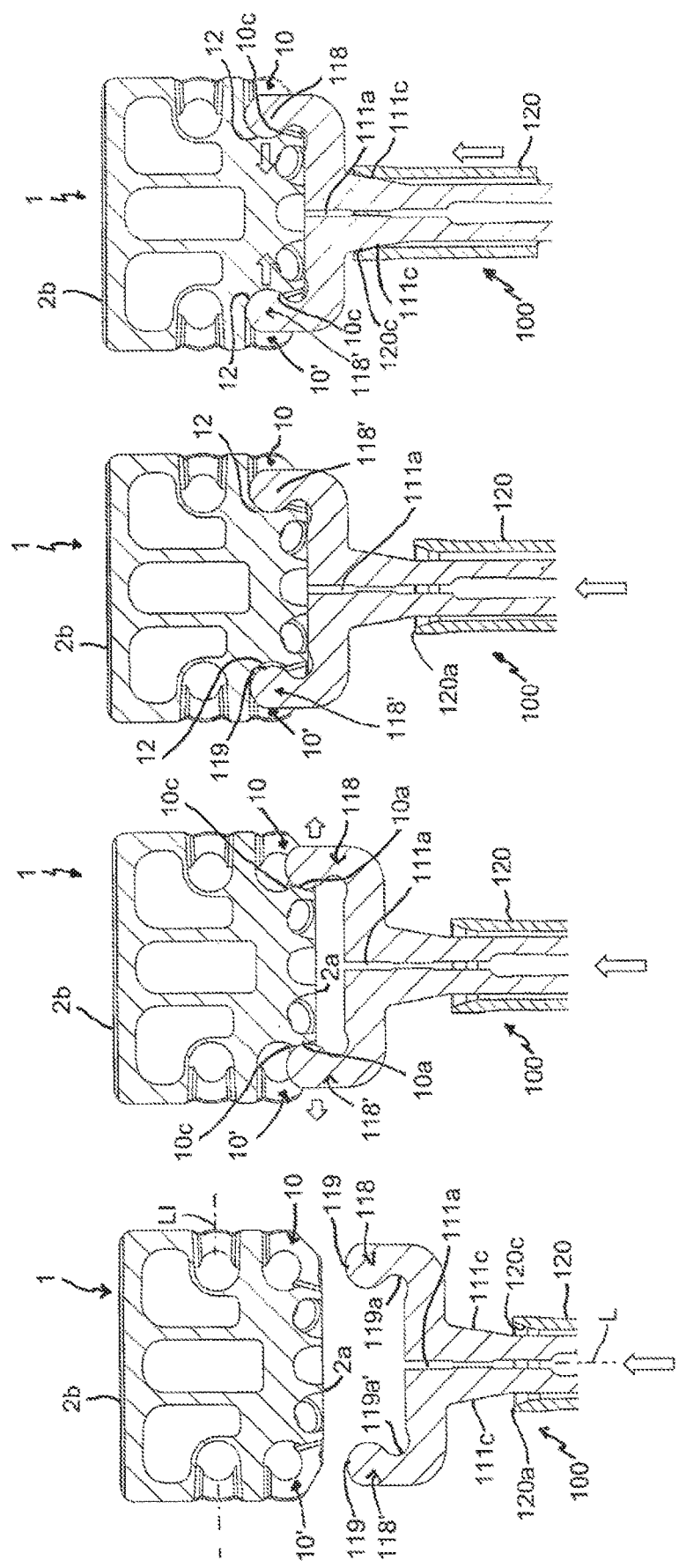
FIGS. 11a to 11d show cross-sectional views of steps of engaging the intervertebral implant with the insertion device according to FIGS. 1, 9, and 10 and locking the intervertebral implant relative to the insertion device.

Referring to FIGS. 11a to 11d, the steps of engagement of the intervertebral implant with the insertion device are shown in more detail. In FIG. 11a, the insertion device is moved towards the front wall 2a with the sleeve 120 in the retracted position. In FIG. 11b the outer spherical segment-shaped ends 119, 119' of the engagement portions 118, 118' move through the openings 11 into the recesses 10, 10', respectively. As they slide along the inclined boundary walls 10a, the holding members 111, 111' are slightly spread apart. As depicted in FIG. 11c, the outer ends 119, 119' of the engagement portion. 118, 118' have entered the spherical recesses 12 and clamp the implant between them. Finally, as shown in FIG. 11d, the sleeve 120 is moved towards the cross-bars 117, 117'. Since the sleeve slides along the tapered portion 111c, the holding members 111, 111' are pressed towards each other so that the outer ends 119, 119' of the engagement portions 118, 118' are firmly pressed against the wall of the recess 12. By means of this, the connection is fixed.

In clinical use, the intervertebral implant of this type may be inserted from an anterior side. Once the intervertebral implant has been placed with the insertion device 100 between two vertebral bodies, the insertion device can be removed. This is effected by holding the holding portion 110 with the handle 30 and retracting the sleeve 120. Thereby, the clamping of the engagement portions 118, 118' is loosened and the engagement portions can be disengaged from the implant.

Since the height of the front portion 112, 112' of the insertion device is smaller than the height of the front wall 2a of the intervertebral implant 1, the visibility of the intervertebral implant during the insertion process may be improved. Also the width of the insertion device is smaller than the width of the implant, which may be helpful during insertion and release of the implant.

Figure 12:
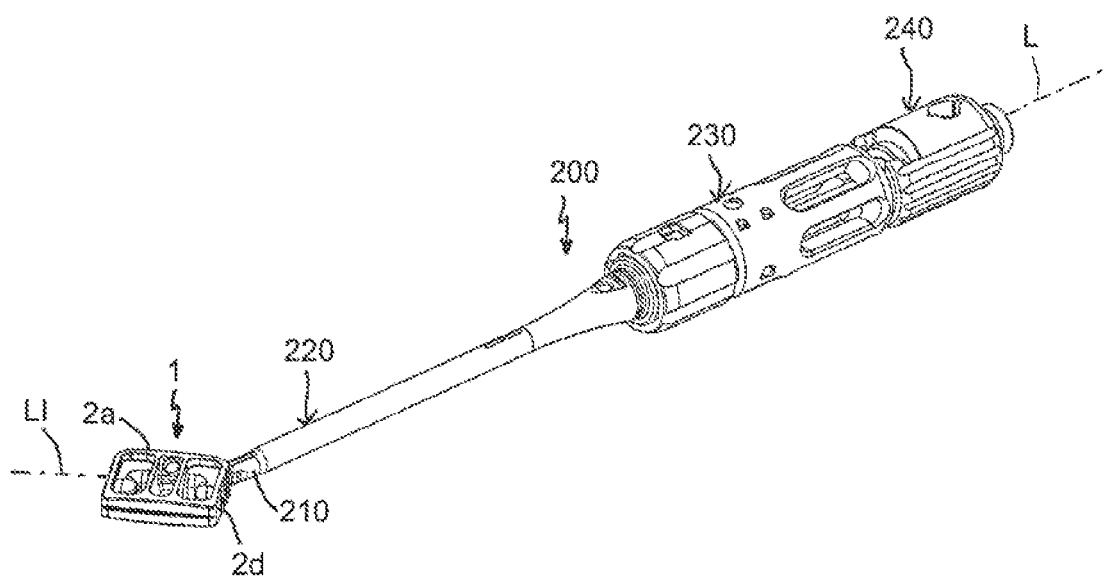
FIG. 12 shows the intervertebral implant of FIGS. 2 to 5 with a second embodiment of an insertion device in a first mode of connection.
Figure 13:
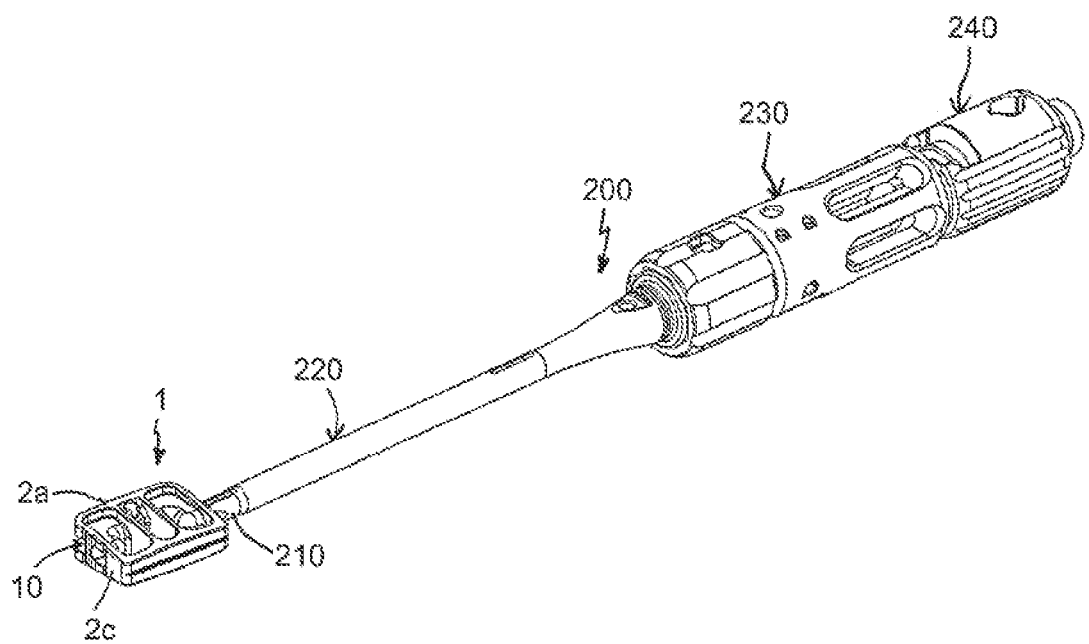
FIG. 13 shows a perspective view of the intervertebral implant and insertion device of FIG. 12 in a second mode of connection.

Referring to FIGS. 12 and 13, the intervertebral implant 1 is shown together with another embodiment of an insertion device. The intervertebral implant 1 in the form of an ALIF-cage has increased functionality due to the connection portions in the form of the recesses 10, 10', 30, 30'. The insertion device 200 is an insertion device which may be used for implants which are inserted between the vertebrae in an antero-lateral or lateral approach, and which may require in some cases a specific angle or a variation of that angle between the insertion device and the intervertebral implant along the insertion trajectory. FIG. 12 shows the insertion device 200 engaging one of the recesses 10, 10' at a corner of the intervertebral implant. FIG. 13 shows the insertion device 200 engaging one of the recesses 30, 30' at the left sidewall or the right sidewall of the intervertebral implant.

Referring now to FIGS. 14 to 19, the insertion device 200 will be described in greater detail. The insertion device 200 includes a holding portion 210, a guiding sleeve 220 that receives the holding portion 210 therein, a handle 230, a rotation actuating member (not shown), and an axial position adjusting device 240. The holding member 210 is movably guided within the guiding sleeve 220 and may be advanced or retracted with respect to the guiding sleeve 220 by actuating the axial position adjusting device 240. Further, the holding member 210 may be rotated by actuating the rotation actuating member. It shall be noted that axial displacement of the holding member 210 and rotating of the holding member 210 may be achieved in various other ways.

Figure 14:
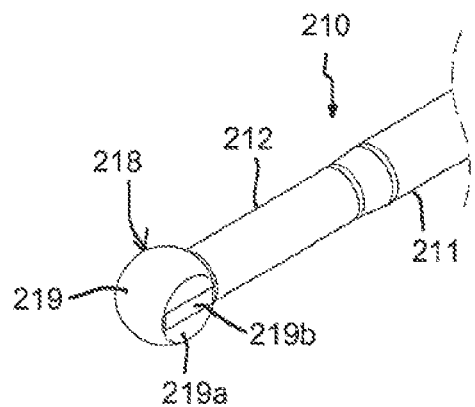
FIG. 14 shows a perspective view from above of a front portion of a holding member of the insertion device of FIGS. 12 and 13.
Figure 15:
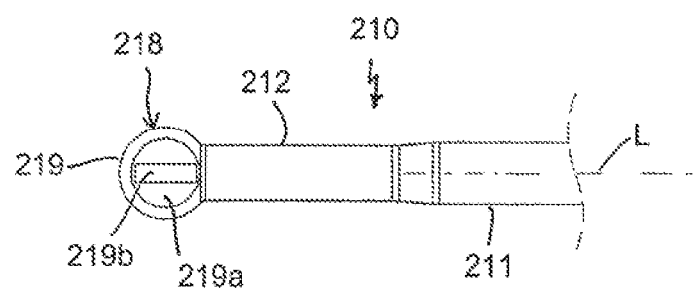
FIG. 15 shows a side view of the holding member of FIG. 14.
Figure 16:
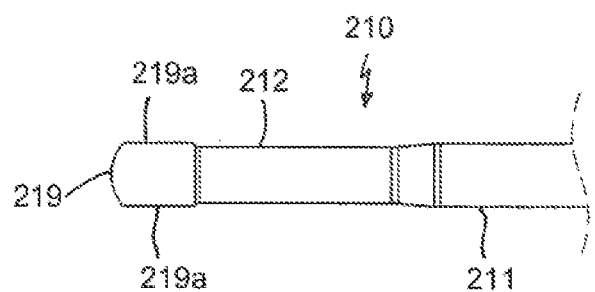
FIG. 16 shows another side view of the holding member of FIGS. 14 and 15.

The holding member 210 defines the longitudinal axis L of the insertion device, and has a front portion which is shown in greater detail in FIGS. 14 to 16. The front portion includes an engagement portion 218 with a spherical surface 219 that has the shape of a segment of a sphere. The spherical surface 219 may be formed by removing opposite segments of the sphere to yield opposite flat surfaces 219a. Hence, the engagement portion 218 has a flattened shape with a thickness between the flat surfaces 219a that is slightly smaller than a vertical height of the elongate opening 11 and heights of the openings 31 of the optional recesses 30, 30'. This permits insertion of the engagement portion 218 into the recesses 10, 10', and optionally into the recesses 30, 30' of the intervertebral implant 1, in an orientation where the flat surfaces 219a extend perpendicular to the height direction of the sidewall 2.

On at least one, and preferably on both, of the flat surfaces 219a, a longitudinally extending positioning mark 219b may be provided, that extends parallel to the longitudinal axis L of the insertion device 200.

The engagement portion 218 is connected to a main portion 211 via a neck portion 212. The neck portion 212 has an outer diameter that is smaller than the maximum diameter of the spherical surface portion 219 of the engagement portion 218. The main portion 211 may have a greater diameter than the neck portion 212. The spherical segment-shaped portion 219 of the engagement portion 218 has a size such that, once the portion 218 has been inserted into the recess 10, 10' and engages the inner spherical recess 12 or into one of the recesses 30, 30' and engages the inner spherical recess 32, the holding member 210 can be tilted by 90°, so that the engagement portion 218 is held in the spherical recess 12 or in one of the spherical recesses 32 but can still pivot therein.

Figure 17:
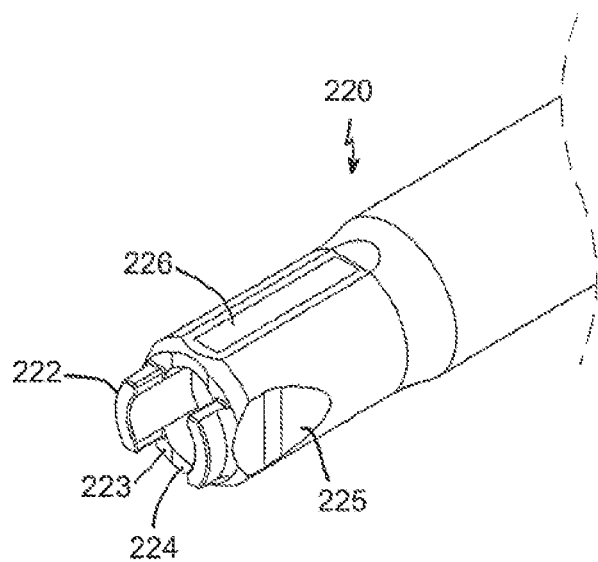
FIG. 17 shows a perspective view of a front portion of a locking sleeve of the insertion device of FIGS. 12 and 13.
Figure 18:
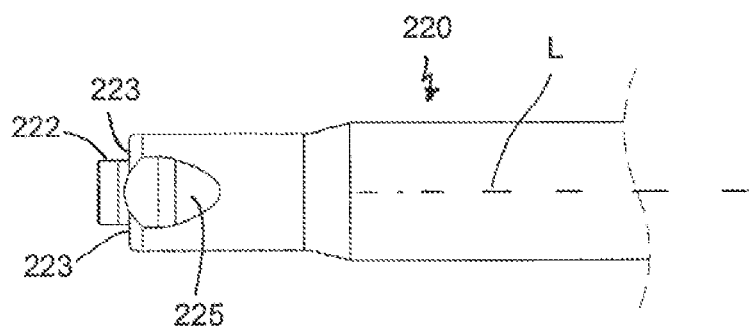
FIG. 18 shows a side view of the locking sleeve of FIG. 17.
Figure 19:
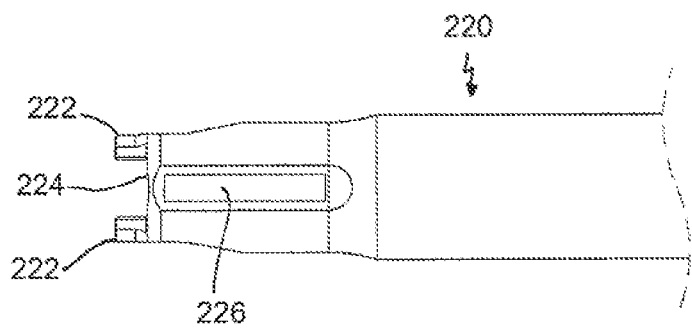
FIG. 19 shows a top view of the locking sleeve of FIGS. 17 and 18.

The front portion of the guiding sleeve 220 is shown in greater detail in FIGS. 17 to 19. When the holding member 210 is arranged in the guiding sleeve 220, the engagement portion 218 protrudes out of the front portion of the guiding sleeve 220. Two opposite cylindrical projections 222 form the outermost end of the guiding sleeve 220. The cylindrical projections 222 have a size such that they are insertable into the recesses 10, 10', 30, 30', respectively. An end face of the tubular guiding sleeve 220 includes a planar surface 223 and a concave, and more specifically, a cylindrical surface 224 that is arranged between the two projections 222 and that has a cylinder axis which is perpendicular to the longitudinal axis L. The planar surface 223 thus forms adjacent each projection 222 an abutment surface for abutting against the second abutment surface 22 or the third abutment surface 23 at the sidewall 2 of the intervertebral implant 1 when the guiding sleeve 220 is pressed against the sidewall 2. The cylindrical surface 224 forms a small guiding surface that is configured to cooperate with guiding surface 24 at the sidewall 2 of the intervertebral implant 1 to permit a guided rotational movement of the intervertebral implant relative to the insertion device in an angular range. Hence, a radius of the cylindrical guiding surface 224 corresponds, for example, to a radius of the cylindrical guiding surface 24 on the left sidewall 2d of the intervertebral implant 1.

At an outer wall of the guiding sleeve 220 adjacent to the cylindrical projections 222 in a longitudinal direction, two opposite positioning flat surfaces 225 may be provided. The positioning flat surfaces 225 indicate the position of the cylindrical projections 222, and may serve for orienting the insertion device 200 correctly during connection with the intervertebral implant 1. Moreover, at least one longitudinally extending positioning mark 226 at an outside of the front portion of the guiding sleeve 220 may further be provided that is 90° offset from the positioning flat surfaces 225 and that may also help indicate the position of the projections 222.

When the holding member 210 is inserted into the guiding sleeve 220 and the engagement portion 218 projects out of the front portion of the guiding sleeve 220, the holding member 210 may be pushed forward and retracted by actuating the axial position adjustment device 240. The size of the projections 222 is such that the engagement portion 218 can only be retracted between the projections 222 in a 90° upright position of the engagement portion 218.

The intervertebral implant 1 and the insertion device may be manufactured from the same materials as described before with respect to the intervertebral implant 1 and the insertion device 100.

Next, the operation of the intervertebral implant 1 and the insertion device 200 will be explained, referring to FIGS. 20 to 22d. The various connection possibilities provided by the recesses 10, 10', 30, 30' increase the possibilities for surgical approaches for insertion of the intervertebral implant 1. First, with reference to FIGS. 20 to 22d, an angled connection will be described, in which the intervertebral implant 1 and the insertion device 200 are connected via the recesses 10 or 10' at the corner of the implant. This connection permits adjustments to the angular position between the intervertebral implant 1 and the insertion device 200.

Figure 20:
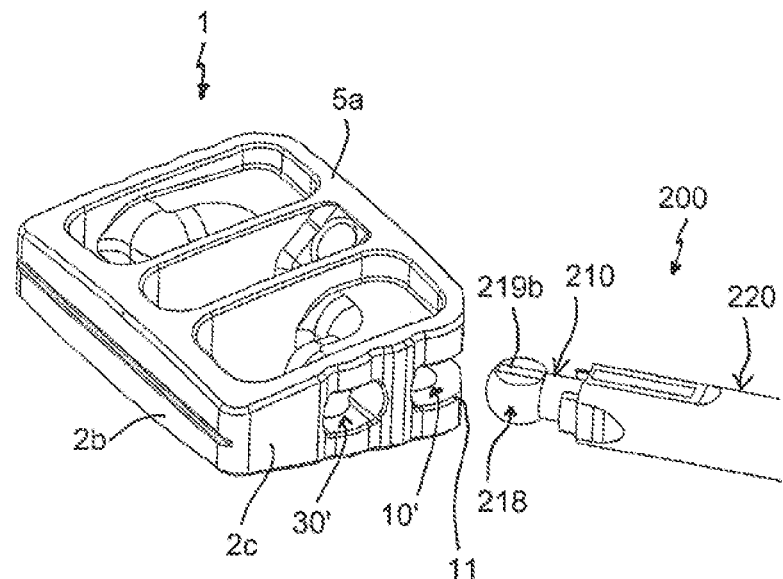
FIG. 20 shows a perspective view of a step of orienting the intervertebral implant and the insertion device of FIG. 12 relative to each other.
Figure 21:
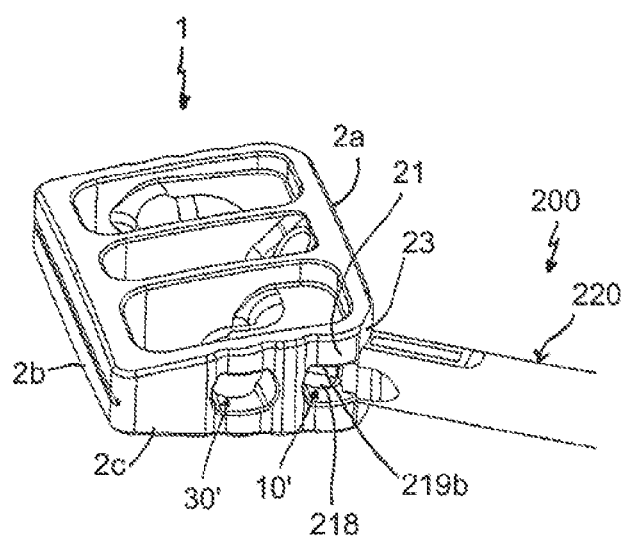
FIG. 21 shows a second step of engaging the intervertebral implant of FIG. 20 with the insertion device.

As depicted in FIG. 20, the intervertebral implant 1 and the insertion device 200 are oriented towards each other in a manner such that the engagement portion 218 faces towards the recess 10' at the corner, between the front wall 2a and the left sidewall 2c. The engagement portion 218 is oriented such that the flat top and bottom surfaces 219a are substantially perpendicular to the axis of rotation R of the intervertebral implant 1. The marking 219b faces towards the upper rim of the opening 11, which facilitates the proper orientation of the engagement portion 218. As illustrated in FIG. 21, in this orientation, the engagement portion 218 can be inserted through the opening 11 into the recess 10' until the engagement portion 218 abuts against the inner wall of the spherical recess 12. Then, the engagement portion 218 is rotated until the flat surfaces 219a extend parallel or substantially parallel to the axis of rotation R. In this configuration, the engagement portion 218 is prevented from being removed through the opening 11. For locking the connection, the guiding sleeve is advanced such that the cylindrical projections 222 extend into the recess 10' through the opening 11. In FIG. 21, the flat abutment surfaces 223 of the guiding sleeve 220 abut against the flat abutment surface 23 surrounding the opening, as shown for example in FIGS. 2 and 3, so that the angle between the longitudinal axis L of the insertion device 200 and the central axis LI of the intervertebral implant 1 is about 45°. The holding member 210 is pulled backward and fixed in the pulled back position to lock the parts together. The connection may be locked by actuating a locking mechanism that holds the guiding sleeve 220 in this position.

Figure 22A:
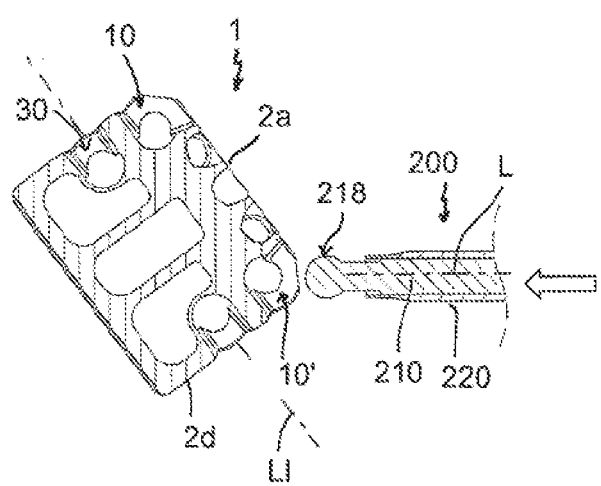
FIGS. 22a to 22d show cross-sectional views of engaging the intervertebral implant with the insertion device as shown in FIG. 12 in the first mode of connection in various pivot positions of the intervertebral implant relative to the insertion device.
Figure 22B:
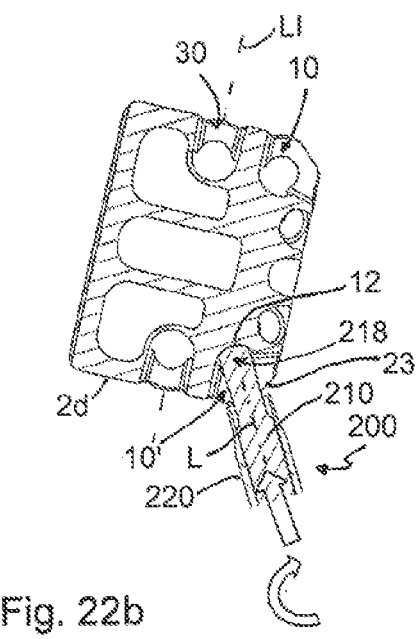
Figure 22C:
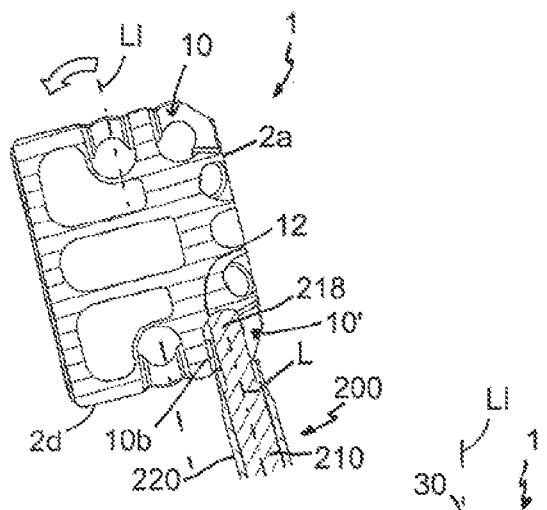
Figure 22D:
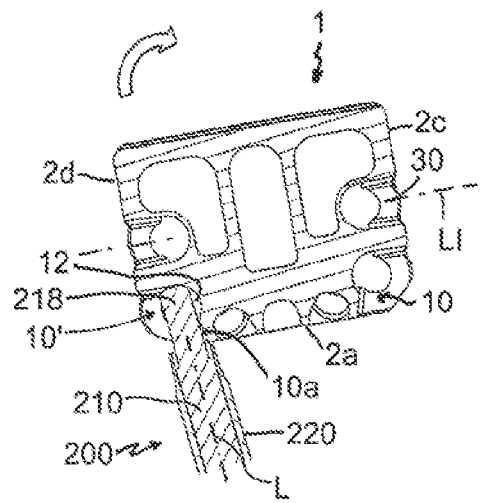

FIGS. 22a and 22b show in a cross-sectional view the relationship between the intervertebral implant 1 and the insertion device 200 during the insertion and fixation step. Hence, FIG. 22a shows a proper orientation before inserting the engagement portion 218 into the recess 10', and FIG. 22b corresponds to the position in which the engagement portion has been rotated by 90° within the recess 12. In FIG. 22c, the connection portion 218 is rotated in the spherical recess 12 until one of the flat surfaces 219a abuts against the boundary wall 10b of the recess 10', so that the insertion device 200 extends away from the left sidewall 2c of the intervertebral implant. In this configuration, the insertion device and the intervertebral implant form an angle of substantially 0°. In FIG. 22d, the engagement portion 218 is rotated in the spherical recess 12 until the other one of the flat surfaces 219a abuts against the boundary wall 10a of the recess 10', such that the insertion device extends from the front wall 2a of the intervertebral implant 1. In this configuration, the angle between the intervertebral implant 1 and the insertion device is a little more than 90°, due to the inclination of the boundary wall 10a with respect to the front wall 2a.

Figure 22E:
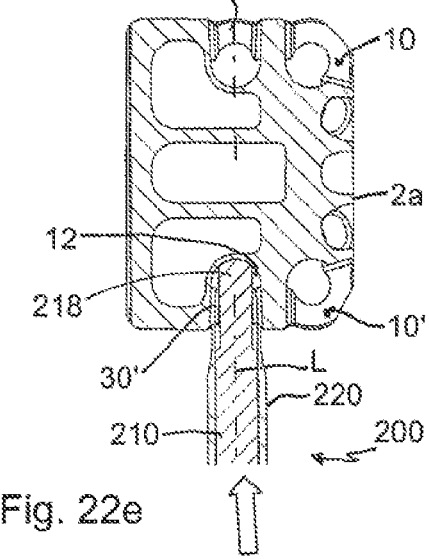
FIG. 22e shows a cross-sectional view of engaging the intervertebral implant as shown with the insertion device as shown in FIG. 13 in the second mode of connection.
Figure 23:
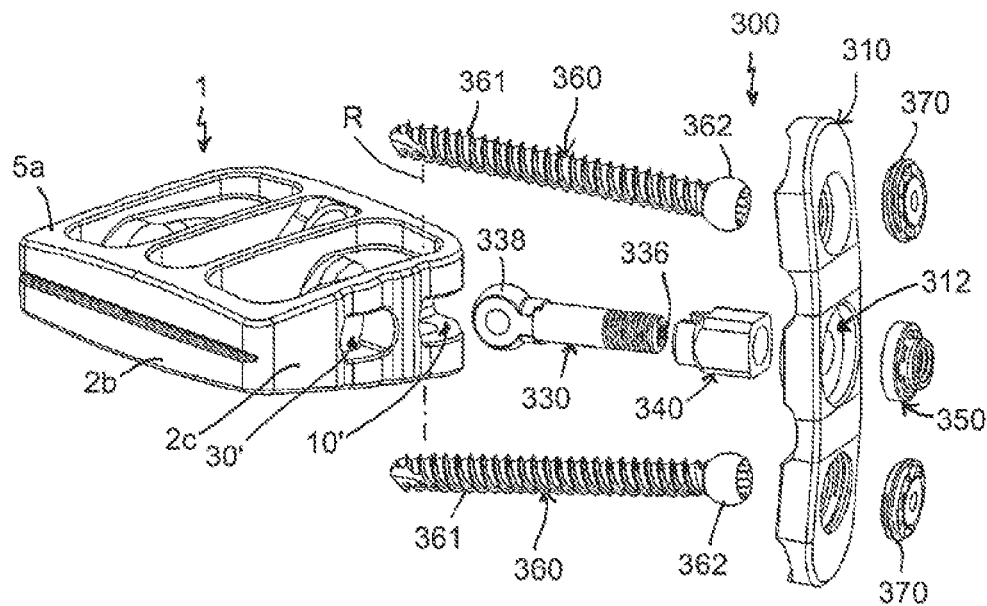
FIG. 23 shows an exploded perspective view of the intervertebral implant of FIGS. 2 to 5 together with a plate assembly.

FIG. 22e shows the engagement of the intervertebral implant through the additional recess 30' in left sidewall 2d. In this configuration, the implant and the insertion device can be locked together in a single position.

Generally, in use, when the engagement portion 218 is in the 90° tilted upright position while in the recess 10, 10', the engagement portion 218 is freely pivotable around the rotational axis R, so that a plurality of angular positions of the insertion device 200 relative to the intervertebral implant can be achieved. When the holding member 210 is retracted with the engagement portion 218 being in the upright position, engagement portion 218 presses from inside against a wall of the recess 10 or 10', so that the insertion device and the implant are pulled together. Thereby, various angular positions can be fixed. With the abutment surfaces, predefined angular positions, such as 0°, 90°, or 45° as shown in the exemplary embodiments, can be fixed in a form-fit manner. Intermediate angular positions may also be achieved by the aid of the guiding surfaces 24, 224 and a force-fit connection. Loosening the fixation allows adjustments to the relative position between the intervertebral implant and the insertion device without disconnecting the insertion device from the implant. This may be particularly useful for lateral or anterior approaches to the intervertebral space.

By means of the aforementioned steps and with a suitable combination of the intervertebral implant and the appropriate insertion device, various access paths to an intervertebral space can be realized with one single type of intervertebral implant. In particular, an ALIF intervertebral implant may in some situations be inserted from the anterior side with the insertion device 100, and in other situations laterally using the insertion device 200.

Only by way of example, in a surgical method, access is made to the damaged disc, the disc is removed, and the intervertebral implant filled with bone graft is inserted. The spinal segment is then stabilized, for example, using pedicle screws and rods. The intervertebral implant and the insertion devices according to embodiments of the invention provide for a variety of possibilities to engage the intervertebral implant and to insert the intervertebral implant into the intervertebral space. Once the intervertebral implant is finally implanted in the intervertebral space, the insertion device is removed.

Referring to FIGS. 23 to 37, an embodiment including the intervertebral implant and a plate assembly will be described. The intervertebral implant 1 is in this embodiment the same as in the previous embodiments. The plate assembly 300 includes a plate member 310 that is connectable to the intervertebral implant 1 via a holding member 330, a sleeve 340, and a locking member 350. The plate assembly 300 further includes bone fixation members 360 in the form of bone screws that are configured to engage the adjacent vertebrae between which the intervertebral implant 1 is sandwiched. The bone fixation members 360 each may be secured against backing out using locking members 370.

The plate member 310 will be described in greater detail, referring to FIGS. 25 to 28. The plate member 310 has an elongate shape with a top surface 310a and an opposite bottom surface 310b. It shall be understood that the plate member can have any shape, however, the elongate shape shown may be useful for application along the spinal column. End portions 310c, 310d of the plate member may be rounded, more specifically may have a substantially cylindrical outer contour. In addition, the plate member 310 may have a shallow curvature along its length, so that the plate member is slightly convexly shaped in a direction away from the intervertebral implant in a connected state. At a distance from the end portions 310c, 310d, two holes 311 are provided that serve for guiding through the fixation members 360, respectively. The holes 311 each have, adjacent the bottom surface 310b, a threaded portion 311a that is configured to cooperate with a thread on the shank 361 of the fixation member 360. A side recess 311b is provided at respective sides of the threaded portion 311a that face towards the outer ends 310c, 310d. The side recesses 311b permit the shank 361 of the fixation members 360 to be oriented outward in an oblique manner to enable insertion into a portion of the adjacent vertebra. Adjacent to the top surface 310a, each of the holes 311 includes a recess 311c with a greater diameter than that of the threaded portion 311a, which serves for housing a head 362 of the fixation member 360, respectively, and for accommodating the locking member 370. The recess 311c may have in at least a portion thereof an inner thread that cooperates with an outer thread of the locking member 370.

Between the holes 311, a central hole 312 is provided that is located substantially at a middle of the plate member 310 in the longitudinal direction. In the region of the central hole 312, the bottom surface 310b includes a substantially flat portion 313 that may serve as an abutment for the sleeve 340. Adjacent to the abutment, a first unthreaded portion 312a of the central hole 312 is formed that is substantially cylindrical and has an inner diameter that permits a portion of the holding member 330 to extend therethrough. At the opposite side a substantially cylindrical threadless recess 312b forms part of the hole 312 which has a greater diameter than the threadless portion 312a. The threadless recess 312b serves for accommodating at least a portion of the locking member 350.

Figures 29, 30:
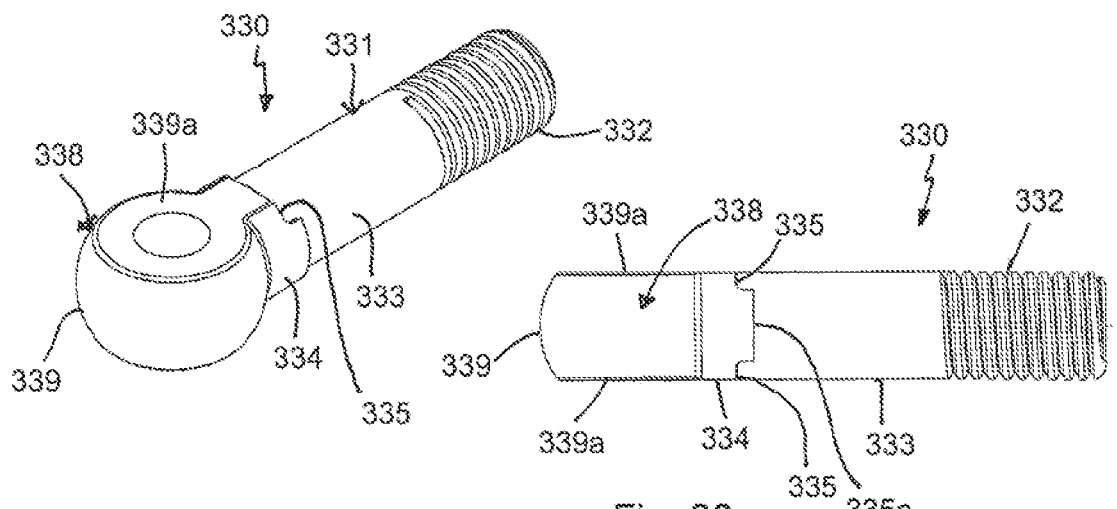
FIG. 29 shows a perspective view from a top of a holding member of the plate assembly of FIGS. 23 and 24.
FIG. 30 shows a side view of the holding member of FIG. 29.
Figure 31:
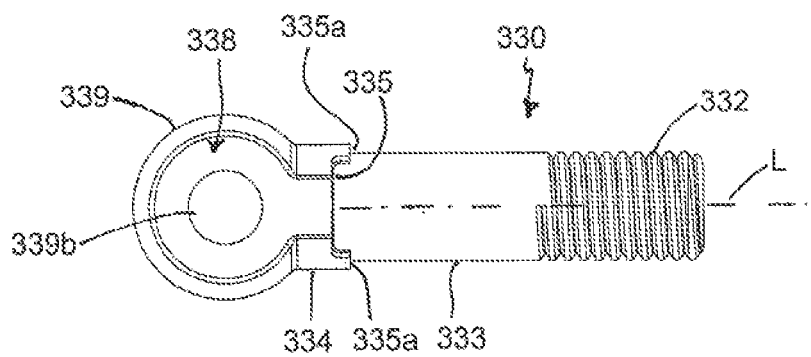
FIG. 31 shows a top view of the holding member of FIGS. 29 and 30.
Figures 32, 33:
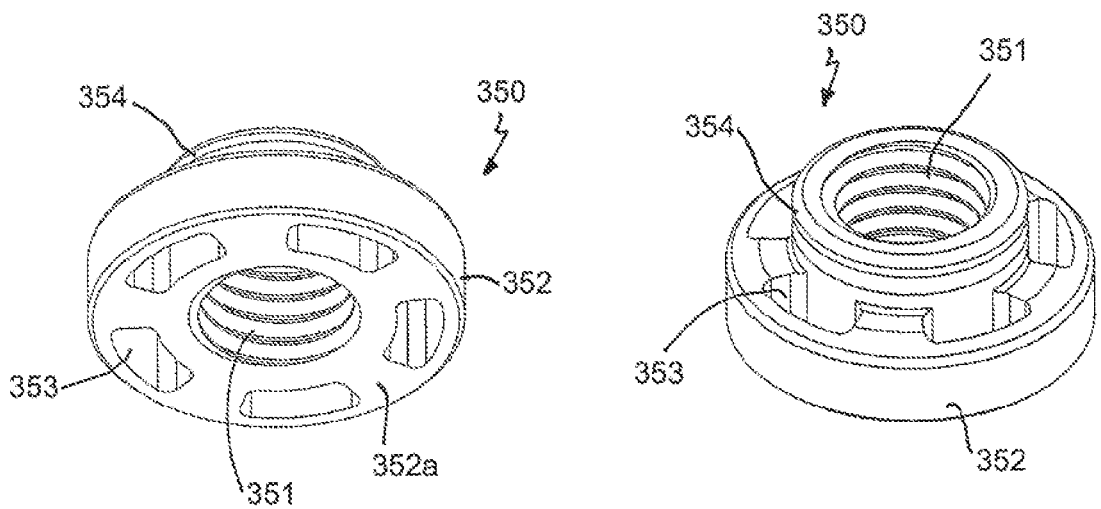
FIG. 32 shows a perspective view from a top of a locking member of the plate assembly of FIGS. 23 and 24.
FIG. 33 shows a perspective view from a bottom of the locking member of FIG. 32.
Figure 34:
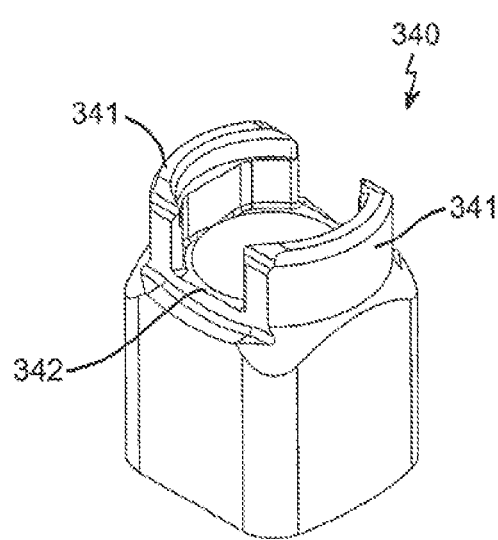
FIG. 34 shows a perspective view from a top of a sleeve member of the plate assembly of FIGS. 23 and 24.
Figure 35:
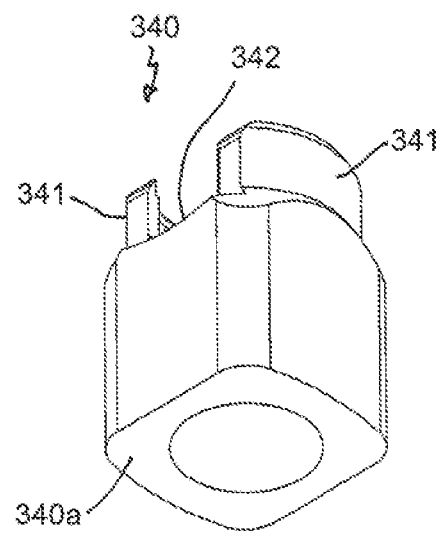
FIG. 35 shows a perspective view from a bottom of the sleeve member of FIG. 34.
Figure 36:
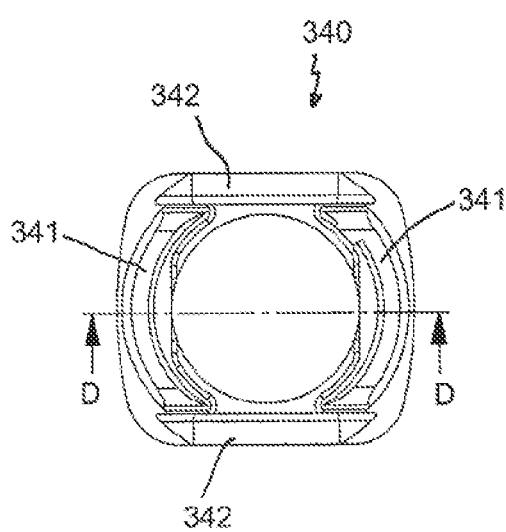
FIG. 36 shows a top view of the sleeve member of FIGS. 34 and 35.
Figure 37:
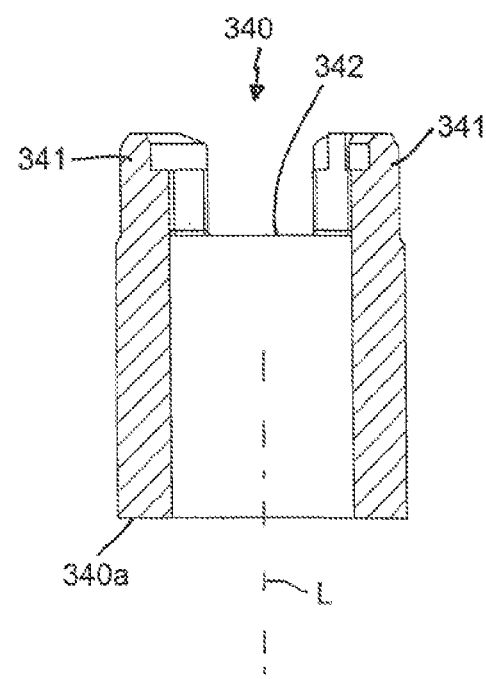
FIG. 37 shows a cross-sectional view of the sleeve member of FIGS. 34 to 36, the cross-section taken along line D-D in FIG. 36.

The holding member 330 will be explained in greater detail, referring to FIGS. 29 to 31. The holding member 330 includes an engagement portion 338 that is shaped substantially as a segment of a sphere, with a spherical outer surface 339 and flat top and bottom surfaces 339a. The shape of the engagement portion 338 is very similar to the shape of the engagement portion 218 of the insertion device according to FIGS. 14 to 16. Hence, the engagement portion 338 is configured to engage the recesses 10, 10' or 30, 30' in the same manner as the engagement portion of the insertion device 200. A marking 339b may be provided at at least one of the flat top or bottom surfaces 339a of the engagement portion 338. If the holding member 330 is oriented with the marking 339b facing toward the upper rim of the opening 11 of the recess 10, the holding member 330 is in the correct orientation for insertion. The engagement portion 338 is connected, for example monolithically, to a rod or bar 331. The bar 331 has a threaded end portion 332 opposite to the engagement portion 338. Between the engagement portion 338 and the threaded end portion 332, a thread-free section 333 is provided on which the sleeve 340 is placed. Between the engagement 338 and the thread-free section 333 of the holding member 330, a thickened section 334 may be provided that has a slightly greater outer diameter than the thread-free section 333. The thickened section 334 has an edge 335 from which two projections 335a, offset by 180°, extend that are configured to enter between two projections of the sleeve 340. The length of the rod portion 331 of the holding member 330 is such that, when the sleeve 340 is mounted thereon, the threaded end portions 332 extends through the first unthreaded portion 312a of the central hole 312 of the plate member 310 into the recess 312b, in order to be engaged by the locking member 350. At the threaded end portion 332 of the holding member, a coaxial hole 336, preferably with an internal thread, may be used for connecting an insertion device such as a threaded rod thereto (not shown).

The locking member 350 is a nut-like member having a central threaded hole 351 in which the threaded end portion 332 of the holding member can be screwed. Around the central threaded hole 351, a cylindrical rim 352 is formed that has a size such that the locking member fits into the recess 312b of the central hole 312 provided in the plate member 310. In addition, a plurality of elongate circumferentially arranged pockets 353 are provided that extend completely through the cylindrical rim 352 and that serve for engagement with a drive tool. Opposite to the lower side 352a of the cylindrical rim 352, the nut-like member includes a cylindrical portion 354 with a smaller outer diameter. The length of this portion is such that once the locking member 350 is in the recess 312b of the central hole 312, the cylindrical portion 354 extends out of the top surface 310a of the plate member, so that it can be detected more easily with a tool.

Referring to FIGS. 34 to 37, the sleeve member 340 will be described. The sleeve member is configured to be placed onto the thread-free portion 333 of the holding member 330. A rear end 340a of the sleeve member 340 is substantially flat and is configured to abut against the flat surface portion 313 of the plate member 310. The front portion of the sleeve member has two substantially cylindrical projections 341 that are offset by 180° and configured to extend through the opening 11 into the recesses 10, 10' or 30, 30' of the intervertebral implant 1. Between the projections 341, an abutment surface 342 is formed that is configured to cooperate with an abutment surface at the intervertebral implant, for example with the abutment surface 23 in the corner of the intervertebral implant. An outer contour of the sleeve 340 may be substantially square-shaped with rounded edges. Any other contour, for example a cylindrical shape may also be possible. The projections 335a of the holding member 330 are configured to fit in-between the projections 341 of the sleeve member 340. It shall be noted that the sleeve and the plate member can also be monolithic.

Figure 24:
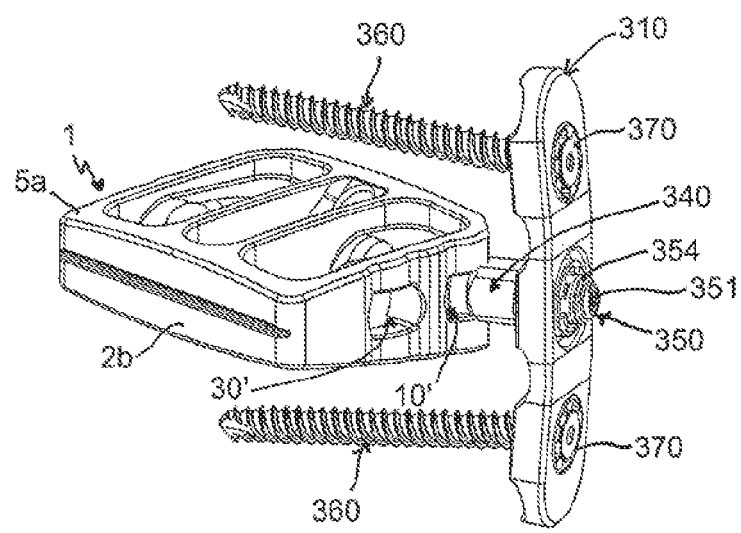
FIG. 24 shows the intervertebral implant and the plate assembly of FIG. 23 in an assembled configuration.
Figure 25:
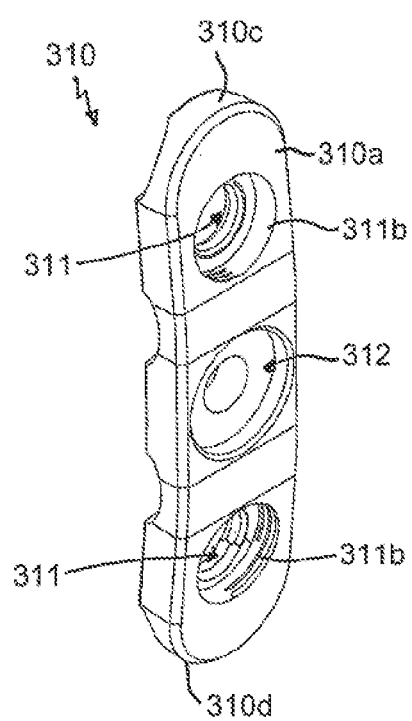
FIG. 25 shows a perspective view from a top of a plate member of the plate assembly of FIGS. 23 and 24.
Figure 26:
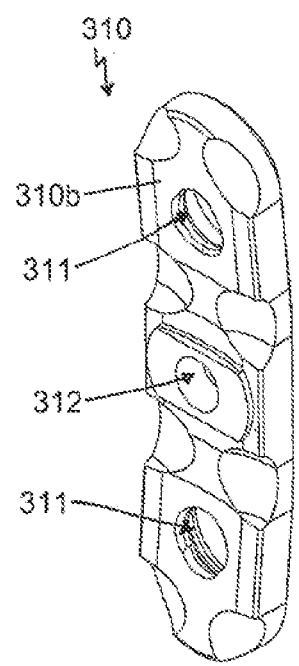
FIG. 26 shows a perspective view from a bottom of the plate member of FIG. 25.
Figure 27:
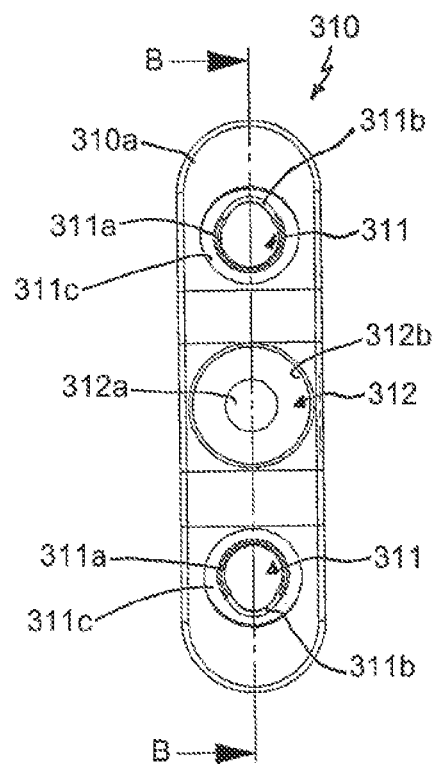
FIG. 27 shows a top view of the plate member of FIGS. 25 and 26.
Figure 28:
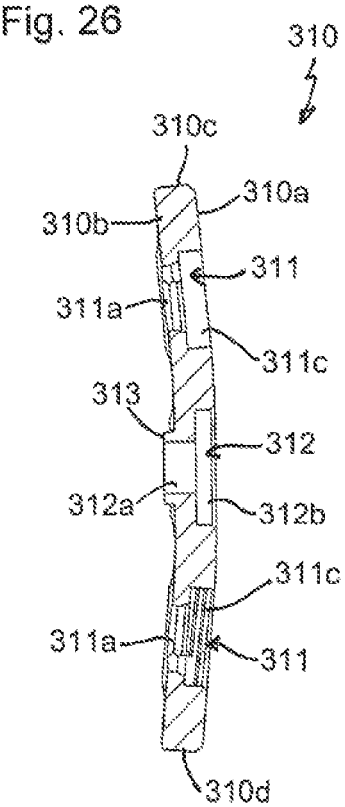
FIG. 28 shows a cross-sectional view of the plate member of FIGS. 25 to 27, the cross-section taken along line B-B in FIG. 27.

In the assembled state, the sleeve 340 is mounted onto the rod-like portion 331, specifically onto the threadless section 333 of the holding member 330, and the threaded end portion 332 is guided through the central hole 312 of the plate member 310 until it projects into the recess 312b. Then the locking member 350 is screwed onto the threaded end portion 332 to connect the holding member 330 to the plate member 310. For connecting the plate assembly to the intervertebral implant after the implant has been inserted into the intervertebral space, the engagement portion 338 is oriented such that the flat surfaces 339a extend substantially parallel to the axis of rotation of the spherical recess 12. Once the engagement portion 318 has been introduced into the recess 10, 10' or 30, 30' through the openings 11 or 31, the engagement portion 338 is tilted by 90° so that it cannot be removed through the openings 11 or 31. Moreover, the holding member 330 is moved backward so that the engagement portion 338 abuts against the inner wall of the recess 10, 10', 31 or 31'. The projections 335a move into the space between the projections 341 of the sleeve member 340, and thus inhibit rotation of the engagement portion 338. Thereafter, the locking member 350 is tightened with respect to the holding member 330, so that the sleeve 340 is firmly pressed with its abutment surface 340a against the flat surface 313 of the plate member and with the abutment surface 342, for example, against the abutment surface 23 of the intervertebral implant, as depicted in FIG. 24. For manipulating the holding member 330, such as insertion into the recess 10 and rotation, a relatively thin at least partially threaded rod may be guided through the locking member 350 and inserted into the threaded hole 336 of the holding member 330.

Due to the threadless connection, the plate member 310 can be easily and quickly connected to the intervertebral implant 1. In addition, as in the previous embodiments, various angles can be adjusted between the holding member 330 and the intervertebral implant 1, depending on the selection of the recess 10, 10', 30 or 30'. In this way, the plate member can assume various orientations with respect to the intervertebral implant, which enhances the possibilities of temporary stabilization. The plate member 310 may be additionally fixed by the bone fixation members 360 which are inserted into the holes 311 and screwed into a portion of the vertebra. The locking members 370 may be used to press onto the heads 362 of the fixation members 360.

In one method of use, the plate member 310 remains implanted. The plate member 310 can also serve for a temporary fixation and can be later removed. Once the bone fixation members 360 have been removed, the unlocking of the holding member 330 from the intervertebral implant 1 can be achieved easily by slightly pushing in the engagement portion 338, tilting the engagement portion, and withdrawing the engagement portion from the recess 10, 10' or 30, 30'.

Figure 38:
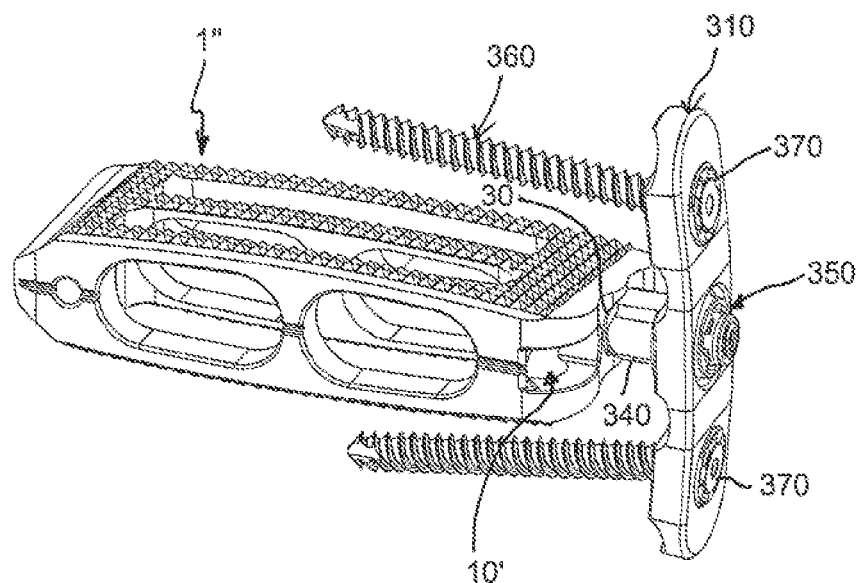
FIG. 38 shows a perspective view of the plate assembly of FIGS. 23 and 24 with another embodiment of a spinal implant in the form of another intervertebral implant.

FIG. 38 shows a further embodiment including an intervertebral implant together with the plate assembly 300. The intervertebral implant 1' in this case is a lateral cage which is elongate and has the recesses 10, 10' for connection with the insertion device and/or the plate member only on one of the short sides of the elongate implant. For example, a single recess 10 may be provided at a corner between a long side and a short side of the implant, and a single recess 30 on the short side may be provided which is used in the depicted embodiment for connection to the plate member 310.

Figure 39:
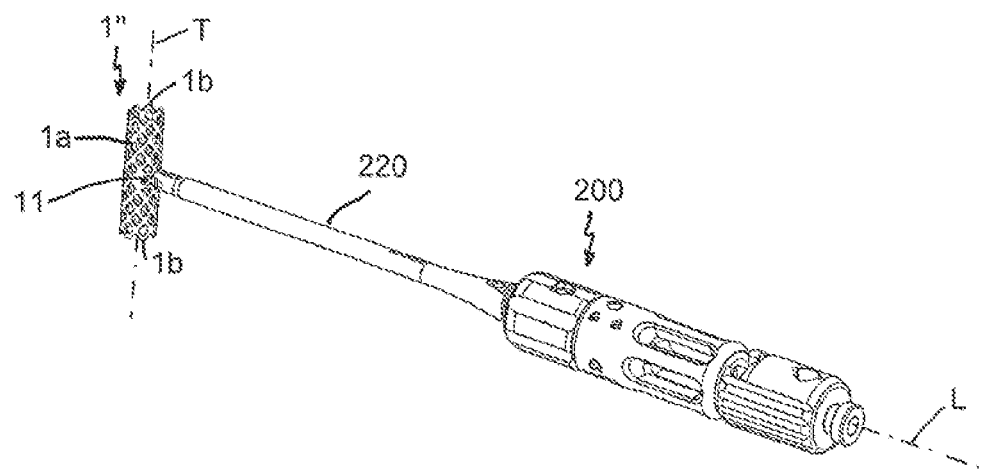
FIG. 39 shows a perspective view of a still further embodiment of a spinal implant with an insertion device, the implant being in the form of a placeholder, for example, used following vertebrectomy.
Figure 40:
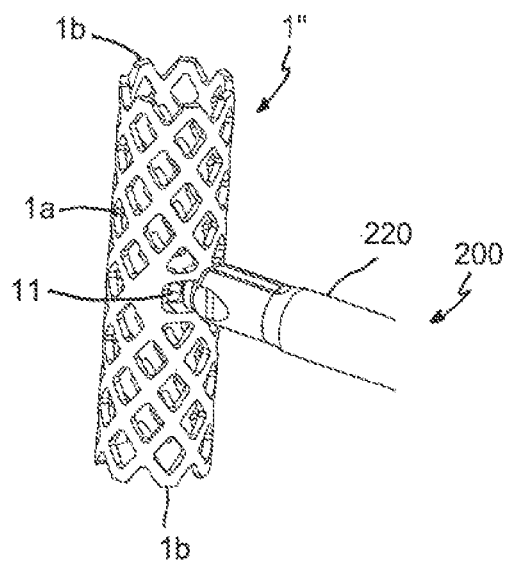
FIG. 40 shows an enlarged perspective view of a portion of FIG. 39.
Figure 41:
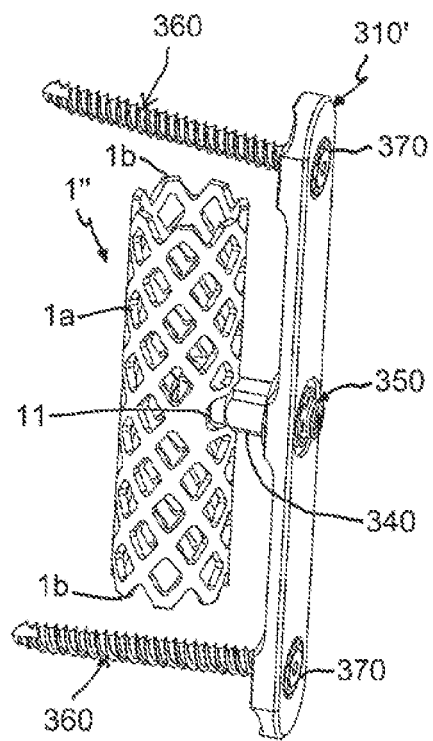
FIG. 41 shows a perspective view of the placeholder of FIGS. 39 and 40 together with the plate assembly of FIGS. 23 and 24.

FIGS. 39 to 41 show a further embodiment of the spinal implant in the form of a placeholder 1" for a vertebra or portions thereof. The placeholder includes a cylindrical tube with a tube axis T and with openings 1a in a wall of the placeholder. Prongs 1b may be formed at either end to engage the end plates of the vertebral bodies between which the placeholder 1" is placed.

In the wall of the placeholder 1", there is an opening 11 that is elongate in the circumferential direction. The inside of the tube behind the opening 11 provides a hollow space for receiving an engagement portion of an insertion device or of a plate assembly.

As can be seen in FIGS. 39 and 40, the placeholder 1" can be used together, for example, with the insertion device 200 according to FIGS. 12 to 19. The engagement portion 218 is inserted in an orientation in which the flat surfaces 219a are perpendicular to the cylinder axis of the tube. After insertion, the engagement portion is tilted by 90° so that the engagement portion is prevented from being removed through the opening 11. Then, the sleeve 220 is advanced to press against the outer wall of the tube and is fixed in this position. Thereafter, the placeholder 1" can be inserted between two vertebrae.

FIG. 41 shows a connection between a plate member 310' and the placeholder 1". The principle of the connection is the same as described with respect to the connection between the placeholder 1" and the insertion device. Depending on the clinical situation, a shorter holding member 330' may be used and the plate member 310' may be straight, i.e., without curvature.

Various other modifications of the spacer and/or the insertion device and/or the plate assembly may further be made without departing from the spirit and scope of the invention.

The spinal implant as shown in the above described embodiments is only an example. The contour and shape of the implant may be different according to specific clinical requirements. For example, the implant may also be in the form of a three-dimensional network or grid structure that can be manufactured, for example, by 3D printing techniques. In a further modified embodiment, the implant may be a dummy implant or testing implant that is used for a trial procedure to open the disc space before insertion of a different implant that remains in the body.

The number of connection portions on the implant provided by the recesses may differ. For example, for the first embodiment, it is sufficient that only one of the recesses has a specific inner shape which allows attachment with a different insertion device. The other one of the recesses may be shaped to only provide an abutment for the engagement portion of one type of insertion device.

The number, orientation, and/or abutment surfaces may also vary between different embodiments. In some embodiments, the elongate opening can be at another position than at an edge. Still further, the elongate opening may extend vertically or at an incline. In such a case, the holding portion can correspondingly be inserted in the upright orientation or inclined orientation, and is then tilted. More than two elongate openings may be provided. Also, a number of additional recesses for receiving the insertion device can be more or less than that shown in the described embodiments.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. An intervertebral implant comprising:
   a body insertable into an intervertebral space, the body comprising a first face, a second face connected to and opposite the first face, a central axis that extends between the first and second faces, a width and a length at least as long as the width that extend around the first and second faces, and first and second connection portions configured to connect the implant to a separate holding member;
   wherein the first and second connection portions each includes a hollow space between the first and second faces configured to accommodate an engagement portion of the holding member, the hollow space being accessible from outside the body though an opening formed between the first and second faces, with at least part of the implant that defines the hollow space extending away from the opening towards the first face or the second face such that a height of the hollow space measured in a direction of the central axis is greater than a maximum height of the opening, and with at least another part of the implant enclosing at least part of the hollow space in a direction of the central axis;
   wherein each of the openings is elongate with a length measured around the central axis that is greater than the maximum height of the opening, and where a height of the opening remains substantially constant over a majority of the length of the opening, and wherein the openings extend away from one another around the implant from a same first side that defines the length of the body to respective second and third sides opposite to one another that define the width of the body and are arranged in a manner such that the first and second connection portions are simultaneously engageable by the engagement portion of the holding member.

2. The intervertebral implant of claim 1, wherein the holding member is a first holding member, and wherein at least one of the first or second connection portions is configured to interchangeably engage a second holding member that is structured differently from the first holding member without the second holding member engaging the other one of the first or second connection portions.

3. The intervertebral implant of claim 2, wherein the hollow space and the opening of the at least one connection portion are configured such that an engagement portion of the second holding member is insertable through the opening into the hollow space at a first orientation, and is prevented from removal through the opening when the engagement portion of the second holding member is at a second orientation different from the first orientation.

4. The intervertebral implant of claim 1, wherein the hollow space of at least one of the first or second connection portions includes a spherical portion.

5. The intervertebral implant of claim 1, wherein the opening has a contour configured to facilitate pivoting of the implant relative to the holding member along a direction of extension of the opening.

6. The intervertebral implant of claim 1, wherein the implant defines two corners at opposite ends of the first side, and wherein the first and second connection portions respectively extend around the two corners.

7. The intervertebral implant of claim 1, wherein the engagement portion of the holding member is substantially fork-shaped to simultaneously engage the first and second connection portions.

8. The intervertebral implant of claim 1, wherein the holding member is a first holding member, and wherein the implant further comprises a third connection portion configured to be engaged by a second holding member different from the first holding member.

9. The intervertebral implant of claim 8, wherein the third connection portion is only engageable with the second holding member at a singe angle.

10. The intervertebral implant of claim 1, wherein at least one of the first or second connection portions is threadless.

11. A kit comprising:
an implant comprising a body insertable into an intervertebral space, the implant comprising a first connection portion with an opening formed in an outer surface of the implant;
a first holding member comprising a first engagement portion; and
a second holding member different from the first holding member and comprising a second engagement portion;
wherein the first and second engagement portions are interchangeably insertable into the opening and engageable with the first connection portion to respectively connect the first holding member or the second holding member to the implant, and wherein an abutment of the first connection portion is configured to restrict disengagement of a connected holding member from the implant in a direction opposite a direction in which the connected holding member is advanced towards the implant to connect to the implant.

12. The kit of claim 11, wherein the implant is an intervertebral implant.

13. The kit of claim 11, wherein the implant is a placeholder for vertebrae or portions thereof.

14. The kit of claim 11, wherein the first connection portion includes a hollow space accessible from outside the body through the opening.

15. The kit of claim 14, wherein at least one of the first or second engagement portions is insertable through the opening into the hollow space at a first orientation, and is prevented from removal through the opening when the at least one engagement portion is at a second orientation different from the first orientation.

16. The kit of claim 14, wherein the hollow space comprises a spherical portion, and wherein when the first or second engagement portion is connected to the first connection portion, an axis of rotation of the connected holding member extending through a center of the spherical portion.

17. The kit of claim 16, wherein the opening is elongate, extends around the axis of rotation, and has a contour configured to facilitate pivoting of the connected holding member relative to the implant about the axis of rotation.

18. The kit of claim 11, wherein the first holding member is formed as part of a first insertion device, and wherein the second holding member is formed as part of a second insertion device different from the first insertion device.

19. The kit of claim 18, wherein the first holding member is configured to simultaneously engage the first connection portion and a second connection portion of the implant, and wherein the second holding member is configured to engage the first connection portion without engaging the second connection portion.

20. The kit of claim 11, wherein the first holding member is formed as part of an insertion device, and wherein the second holding member is formed as part of a plate assembly.

21. The kit of claim 11, wherein the implant further comprises a second connection portion configured to be engaged by at least one of the first holding member or the second holding member.

22. The kit of claim 11, wherein at least one of the first or second holding members is configured to assume a first configuration where the at least one holding member engages the first connection portion while permitting movement therebetween, and is configured to assume a second configuration where the at least one holding member is configured to engage the first connection portion in a fixed manner.

23. A system comprising:
an implant comprising a body insertable into an intervertebral space, the implant comprising a connection portion; and
a plate assembly comprising a plate member and a holding member rotatable relative to one another;
wherein an engagement portion of the holding member is insertable through an opening of the connection portion at a first configuration, and is prevented from removal through the opening when the engagement portion is at a second orientation different from the first orientation, to engage the connection portion in a threadless manner to connect the plate member to the implant.

24. The system of claim 23, wherein the plate assembly further comprises a locking member configured to lock the holding member to the connection portion of the implant.

* * * * *

UNITED STATES PATENT AND TRADEMARK OFFICE
CERTIFICATE OF CORRECTION

PATENT NO. : 12,208,016 B2  
APPLICATION NO. : 17/479376  
DATED : January 28, 2025  
INVENTOR(S) : Timo Biedermann et al.

Page 1 of 1

It is certified that error appears in the above-identified patent and that said Letters Patent is hereby corrected as shown below:

In the Drawings

In Sheet 1 of 16, in Fig. 1, Line 2, delete "Fig" and insert -- Fig. --.

In the Specification

In Column 5, Line 32, delete "by" and insert -- be --.

In the Claims

In Column 17, Line 45, in Claim 9, delete "singe" and insert -- single --.

Signed and Sealed this  
Twenty-ninth Day of April, 2025

Coke Morgan Stewart  
*Acting Director of the United States Patent and Trademark Office*